(12) United States Patent
Theberge et al.

(10) Patent No.: US 9,883,710 B2
(45) Date of Patent: *Feb. 6, 2018

(54) ARTICLES OF MANUFACTURE RELEASING AN ACTIVE INGREDIENT

(75) Inventors: Karine Theberge, La Prairie (CA); Isabelle Goudreault, Montreal (CA); Francois Quirion, Montreal (CA); Gerald Perron, Boucherville (CA)

(73) Assignee: Biomod Concepts Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/855,783

(22) Filed: Aug. 13, 2010

(65) Prior Publication Data

US 2011/0010817 A1 Jan. 20, 2011

Related U.S. Application Data

(63) Continuation of application No. 12/680,836, filed as application No. PCT/CA2009/001012 on Jul. 17, 2009.

(60) Provisional application No. 61/081,911, filed on Jul. 18, 2008.

(51) Int. Cl.
| | |
|---|---|
| *A41D 1/00* | (2006.01) |
| *A61K 8/02* | (2006.01) |
| *A61K 9/70* | (2006.01) |
| *A61K 31/231* | (2006.01) |
| *A61K 8/97* | (2017.01) |
| *A61K 8/92* | (2006.01) |
| *A61Q 19/00* | (2006.01) |
| *A41D 19/00* | (2006.01) |
| *A43B 1/00* | (2006.01) |
| *A43B 17/00* | (2006.01) |
| *A61K 8/55* | (2006.01) |
| *A61L 15/42* | (2006.01) |
| *A61L 15/44* | (2006.01) |
| *D06M 23/08* | (2006.01) |
| *D06M 23/12* | (2006.01) |
| *A61K 9/00* | (2006.01) |
| *A61K 9/16* | (2006.01) |
| *A61M 35/00* | (2006.01) |

(52) U.S. Cl.
CPC .......... *A43B 1/0045* (2013.01); *A43B 17/003* (2013.01); *A61K 8/0208* (2013.01); *A61K 8/0241* (2013.01); *A61K 8/553* (2013.01); *A61L 15/42* (2013.01); *A61L 15/44* (2013.01); *A61Q 19/00* (2013.01); *D06M 23/08* (2013.01); *D06M 23/12* (2013.01); *A61K 9/0014* (2013.01); *A61K 9/1617* (2013.01); *A61K 9/70* (2013.01); *A61K 2800/56* (2013.01); *A61L 2300/602* (2013.01); *A61L 2300/622* (2013.01); *A61L 2300/802* (2013.01); *A61M 35/00* (2013.01)

(58) Field of Classification Search
None
See application file for complete search history.

(56) References Cited

U.S. PATENT DOCUMENTS

| | | | |
|---|---|---|---|
| 4,550,035 A | 10/1985 | Smith | |
| 4,931,201 A | 6/1990 | Julemont | |
| 5,156,843 A * | 10/1992 | Leong et al. | 424/411 |
| 5,550,044 A | 8/1996 | Kosak et al. | |
| 5,593,508 A | 1/1997 | Gatt et al. | |
| 5,618,555 A | 4/1997 | Tokuda et al. | |
| 5,814,031 A | 9/1998 | Monney et al. | |
| 5,820,879 A | 10/1998 | Fernandez et al. | |
| 5,904,932 A * | 5/1999 | De Vringer | 424/450 |
| 5,972,366 A | 10/1999 | Haynes et al. | |
| 6,183,451 B1 | 2/2001 | Mehl, Sr. et al. | |
| 6,284,234 B1 | 9/2001 | Niemiec et al. | |
| 6,342,250 B1 | 1/2002 | Masters | |
| 6,391,453 B1 | 5/2002 | Hansen et al. | |
| 6,709,663 B2 | 3/2004 | Espinoza | |
| 7,456,147 B2 | 11/2008 | Kumar et al. | |
| 2001/0018072 A1 | 8/2001 | Unger | |
| 2002/0006906 A1 | 1/2002 | Stoltz et al. | |
| 2003/0053974 A1* | 3/2003 | Shefer | A61K 8/0204 424/70.11 |
| 2003/0127251 A1 | 7/2003 | Mazorow | |
| 2003/0147962 A1 | 8/2003 | Bernstein et al. | |
| 2003/0207776 A1* | 11/2003 | Shefer et al. | 510/130 |

(Continued)

FOREIGN PATENT DOCUMENTS

| | | |
|---|---|---|
| EP | 0436729 | 7/1991 |
| EP | 1147765 B1 | 5/2006 |

(Continued)

OTHER PUBLICATIONS

Alander, et al., "The shea butter family—the complete emollient range for skin care formulations", Cosmetics and Toiletries Manufacture Worldwide, 2005, 28-32.

(Continued)

*Primary Examiner* — Melissa Fisher

(74) *Attorney, Agent, or Firm* — Baker & Hostetler LLP

(57) ABSTRACT

The present invention relates to articles of manufacture having a formulation distributed therein, wherein the formulation comprises an active agent which manifests a desirable property when released from the articles of manufacture. The present invention also relates to methods for manufacturing these articles of manufacture, to vehicles for applying the formulation to these articles of manufacture, and to perception indicators indicating the presence and the amount of formulation comprising an active agent applied to an article of manufacture.

18 Claims, 16 Drawing Sheets

(56) References Cited

U.S. PATENT DOCUMENTS

| | | |
|---|---|---|
| 2003/0232091 A1 | 12/2003 | Shefer et al. |
| 2004/0062778 A1 | 4/2004 | Shefer et al. |
| 2004/0116018 A1 | 6/2004 | Fenwick et al. |
| 2004/0170670 A1 | 9/2004 | Smith et al. |
| 2004/0191300 A1 | 9/2004 | Fecht et al. |
| 2005/0058700 A1 | 3/2005 | Wachter et al. |
| 2005/0123588 A1 | 6/2005 | Zhu et al. |
| 2005/0136772 A1 | 6/2005 | Chen et al. |
| 2005/0226904 A1 | 10/2005 | Choi et al. |
| 2005/0232890 A1 | 10/2005 | Hoath et al. |
| 2006/0039956 A1 | 2/2006 | Hensen et al. |
| 2006/0088581 A1 | 4/2006 | Blaszczykiewicz et al. |
| 2006/0106546 A1 | 5/2006 | Roberts et al. |
| 2006/0135026 A1 | 6/2006 | Arendt et al. |
| 2006/0165643 A1 | 7/2006 | Lintner |
| 2006/0233845 A1 | 10/2006 | Lukowski et al. |
| 2006/0233866 A1 | 10/2006 | Hauser et al. |
| 2007/0009583 A1 | 1/2007 | Qvist |
| 2007/0059338 A1 | 3/2007 | Knapp |
| 2007/0082033 A1 | 4/2007 | Doeschner et al. |
| 2008/0085983 A1 | 4/2008 | Ahn |
| 2008/0152894 A1 | 6/2008 | Beihoffer et al. |
| 2008/0311167 A1 | 12/2008 | Oronsky et al. |
| 2009/0047314 A1 | 2/2009 | Bochot et al. |
| 2009/0074859 A1 | 3/2009 | Patel |
| 2010/0009894 A1 | 1/2010 | Leclerc et al. |
| 2010/0273760 A1 | 10/2010 | Staniforth et al. |

FOREIGN PATENT DOCUMENTS

| | | | |
|---|---|---|---|
| EP | 1365731 B1 | | 1/2008 |
| FR | 2920667 A1 | | 3/2009 |
| GB | 2454059 | | 4/2009 |
| JP | 2004-124326 | | 4/2004 |
| WO | WO 2000/001416 A1 | | 1/2000 |
| WO | WO 2002/060399 A1 | | 8/2002 |
| WO | WO 03/028599 | | 4/2003 |
| WO | WO 2004/006880 A1 | | 1/2004 |
| WO | WO 2004/052339 A1 | | 6/2004 |
| WO | WO 2006/106546 | | 10/2006 |
| WO | WO 07/071325 A2 | | 6/2007 |
| WO | WO2008/013757 | * | 1/2008 |
| WO | WO 2008/060778 | | 5/2008 |
| WO | WO 2008/068417 | | 6/2008 |
| WO | WO 2008/079806 | * | 7/2008 |
| WO | WO 2008/079806 A2 | | 7/2008 |
| WO | WO 09/105761 A2 | | 8/2009 |
| WO | WO 10/036947 A2 | | 1/2010 |
| WO | WO 2010/006442 | | 1/2010 |

OTHER PUBLICATIONS

Examiner's Report issued by the Canadian Intellectual Property Office dated Dec. 1, 2011 in connection with Canadian Patent Application Serial No. 2,689,472, 3 pages.

Final Office Action issued by the United States Patent and Trademark Office dated Jan. 26, 2012 in connection with U.S. Appl. No. 12/855,778, 11 pages.

Office Action issued by the United States Patent and Trademark Office dated Mar. 31, 2011 in connection with U.S. Appl. No. 12/855,778, 7 pages.

Supplementary European Search Report dated Apr. 14, 2014 in connection with European Patent Application 09797326.7, 9 pages.

Database WPI, Week 200442, Thomson Scientific, London, GB; AN 2004-443910, XP002722347, 2 pages.

"Polytrap 6603 Adsorber", Health Beauty Solutions, 2009, http://www.healthbeautysolutions.com/TDS/TDS%20PT%206603.pdf, accessed Oct. 17, 2012, 1 page.

Office Action dated Feb. 20, 2015 in connection with U.S. Appl. No. 12/680,836; 13 pages.

Michael D. Triplett II., Thesis of Doctor of Philosophy, The Ohio State University, 2004, "Enabling Solid Lipid Nanoparticle Drug Delivery Technology by Investigating Improved Production Techniques", 47 pages.

Korean Patent Application No. 10-2011-7003712; Notice of Preliminary Rejection; dated Dec. 4, 2015; 15 pages.

Embil, et al., "The Microsponge Delivery System(MDS): A Topical Delivery System with Reduced Irritancy Incorporating Multiple Triggering Mechanisms for Release of Actives," Journal of Microencapsulation 13(5), Sep. 1996, pp. 575-585.

International Application No. PCT/CA2009/001012: International Search Report dated Oct. 8, 2009, 4 pages.

International Application No. PCT/CA2009/001012: Written Opinion of the International Searching Authority dated Oct. 8, 2009, 8 pages.

Klee, et al., "Triggered Release of Sensitive Active Ingredients Upon Response to the Skin's Natural pH," Colloids and Surfaces A: Physiochemical and Engineering Aspects, 338(1-3), Apr. 2009, pp. 162-166.

* cited by examiner ated on Mar. 30, 2010, which is the
ARTICLES OF MANUFACTURE RELEASING AN ACTIVE INGREDIENT

CROSS-REFERENCE TO RELATED APPLICATIONS

This application is a continuation of U.S. patent application Ser. No. 12/680,836 filed on Mar. 30, 2010, which is the U.S. National Phase under 35 U.S.C. 371 of International Application No. PCT/CA2009/001012 filed on Jul. 17, 2009, which claims benefit under 35 U.S.C. 119(e) of U.S. Application No. 61/081,911 filed on Jul. 18, 2008. The contents of all these applications are herein incorporated by reference in their entireties.

FIELD OF TECHNOLOGY

The present invention relates to articles of manufacture having a formulation distributed therein, wherein the formulation comprises an active ingredient which manifests a desirable property when released from the articles of manufacture. The present invention also relates to methods for manufacturing such articles and to vehicles for applying the formulation to the articles. Further, the present invention relates to articles of manufacture having perception indicators indicating the presence of a formulation dispersed within the articles.

BACKGROUND

There is a need in the art for articles of manufacture, such as, but not limited to, articles made of woven and non-woven textiles, having an active ingredient distributed therein, wherein the articles of manufacture exhibit a progressive or immediate release of the active ingredient.

There is also a need for formulations that can incorporate one or more active ingredient and permit the progressive release of the active ingredient, and for formulations from which microparticles can be obtained and that can be retained in the interstices or pores of the articles of manufacture.

Additionally, there is a need for a method and identifiers to determine if an article of manufacture has one or more active ingredients dispersed therein and/or to monitor the amount of the active ingredients remaining on or released from the article of manufacture.

SUMMARY OF THE INVENTION

In one aspect, the present invention relates to an article of manufacture, comprising: a substrate; microparticles distributed in at least a portion of the substrate, wherein the microparticles include an active ingredient dispersed within a carrier material, the microparticles undergoing progressive erosion in response to a stimulus to cause gradual release of the active ingredient; the microparticles having a release index of between about 1 and about 20.

In another aspect, the present invention relates to an article of manufacture comprising: a substrate; microparticles distributed in at least a portion of the substrate, wherein the microparticles include an active ingredient dispersed within a carrier material, the microparticles undergoing progressive erosion in response to a stimulus to cause gradual release of the active ingredient; wherein after having been through 20 wash cycles, the article of manufacture still maintains a positive active ingredient release rate.

In another aspect, the present invention relates to an article of manufacture comprising: a substrate; microparticles distributed in at least a portion of the substrate, wherein the microparticles include an active ingredient dispersed within a carrier material, the microparticles undergoing progressive erosion in response to a stimulus to cause gradual release of the active ingredient; wherein the article of manufacture maintains a constant rate of release of the active ingredient between 20 and 40 wash cycles.

In another aspect, the present invention relates to an article of manufacture comprising: a substrate; microparticles distributed in at least a portion of the substrate, wherein the microparticles include an active ingredient dispersed within a carrier material, the microparticles undergoing progressive erosion in response to a stimulus to cause gradual release of the active ingredient; wherein the article of manufacture maintains a constant rate of release of the active ingredient between 10 and 20 wash cycles.

In another aspect, the present invention relates to an article of manufacture comprising: a substrate; microparticles distributed in at least a portion of the substrate, wherein the microparticles include an active ingredient dispersed within a carrier material, the microparticles undergoing progressive erosion in response to a stimulus to cause gradual release of the active ingredient; wherein release of the active ingredient is maintained between 15 and 20 wash cycles at a rate that is about 2 to about 3 times the rate between 30 and 40 wash cycles.

In another aspect, the present invention relates to a method for obtaining microparticles having an active ingredient dispersed therein, comprising: forming a stirred melt of a formulation comprising the active ingredient; and obtaining microparticles from the formulation, wherein the microparticles obtained have the active ingredient dispersed therein.

In another aspect, the present invention relates to a method for preparing an article of manufacture as defined herein, comprising: forming a stirred melt of a preparation comprising the active ingredient; obtaining microparticles from the formulation; wherein the microparticles obtained have the active ingredient dispersed therein; and applying the microparticles to the article of manufacture.

In a further aspect, the present invention relates to a method for delivering an active ingredient to a subject, comprising: obtaining a formulation of microparticles having the active ingredient dispersed therein; wherein the microparticles undergo progressive erosion in response to a stimulus causing gradual release of the active ingredient; transferring the formulation of microparticles to a substrate; and placing the substrate in contact with the subject, wherein contact of the substrate with the subject causes the active ingredient to be delivered to the subject.

In a further aspect, the present invention relates to a method for delivering a therapeutic agent to a subject, comprising: applying microparticles having the therapeutic agent dispersed therein to an article of manufacture; wherein the microparticles undergo progressive erosion in response to a stimulus causing gradual release of the therapeutic agent; and wearing of the article of manufacture by the subject; wherein contact of the article of manufacture with the subject's body causes release of the therapeutic agent to the subject's body.

In a further aspect, the present invention relates to a method for delivering a cosmetic agent to a subject, comprising: applying microparticles having the cosmetic agent dispersed therein to an article of manufacture; wherein the microparticles undergo progressive erosion in response to a stimulus causing gradual release of the cosmetic agent; and wearing of the article of manufacture of by the subject; wherein contact of the article of manufacture with the subject's body causes release of the cosmetic agent to the subject's body.

In a further aspect, the present invention relates to a microparticle for delivery of an active ingredient, wherein the microparticle: is obtained from a formulation comprising a carrier material; has the active ingredient dispersed therein; and undergoes progressive erosion in response to a physical stimulus to cause gradual release of the active ingredient.

In a further aspect, the present invention relates to a microparticle for delivery of an active ingredient, wherein the microparticle is made from stearic acid and palmitic acid and has an active ingredient dispersed therein, the microparticle undergoing progressive erosion in response to a stimulus to cause gradual release of the active ingredient.

In a further aspect, the present invention relates to microparticles for delivery of an active ingredient, wherein one or more of the microparticles have a size in the range from about 0.1 μm to about 200 μm, the microparticles undergo progressive erosion in response to a stimulus to cause gradual release of the active ingredient.

In a further aspect, the present invention relates to microparticles for delivery of an active ingredient, wherein the microparticles have a melting temperature between about 20° C. and about 60° C., the microparticles undergoing progressive erosion in response to a stimulus to cause gradual release of the active ingredient.

In a further aspect, the present invention relates to a formulation for obtaining microparticles, comprising a carrier material, a binding agent and a surfactant, wherein the carrier material includes a lipid, a fatty acid-based lipid, a fatty acid or a glyceride or any combination thereof.

In a further aspect, the present invention relates to an application vehicle for transferring microparticles to a substrate, comprising: a support, microparticles applied to the support; wherein the microparticles include an active ingredient dispersed therein, the microparticles undergoing progressive erosion in response to a stimulus to cause gradual release of the active ingredient; wherein when the support is placed in contact with the substrate, the microparticles are transferred from the support to the substrate.

BRIEF DESCRIPTION OF THE FIGURES

In FIG. 3A, the microparticles are obtained from a LASA formulation. In FIG. 3B, the microparticles are obtained from a LASAKAR formulation. In FIG. 3C, the microparticles are obtained from a TPMAGMS formulation. The term "ini" refers to the initial amount of formulation applied to the substrate. The formulations may be provided with binding agent or may be free of binding agent.

FIG. 10A shows a PPFV support assembly onto which a pattern of fiber glass has been applied, without formulation and FIG. 10B shows the trace left by the application of a formulation on a polyester substrate using the PPFV support assembly.

Figure 1:
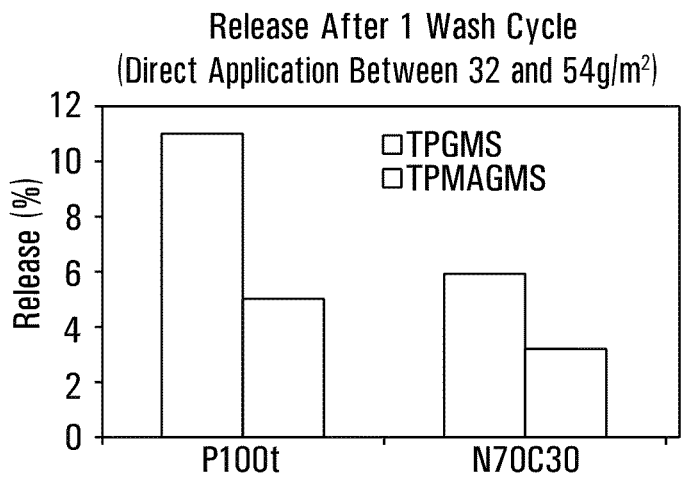
FIG. 1 is a graph showing the release of microparticles, obtained from a TPGMS or a TPMAGMS formulation, from a polyester substrate (P100t) and from a nylon-cotton substrate (N70C30), in accordance with a non-limiting example of implementation of the invention.

FIG. 13 is a schematic representation of an undergarment on which repetitive circles of formulation have been applied to its interior surface, which surface is in contact with the skin of the wearer.

DETAILED DESCRIPTION

The implementations defined below are not intended to be exhaustive or to limit the scope of the application to the precise forms disclosed in the following detailed description.

I. Microparticles

Microparticles as defined herein are not limited to any particular geometric shape and can for example be in the form of globules, bits, droplets, may have a spherical shape, an elliptical shape or may have an irregular or discontinuous shape.

The shape of the microparticle may be irregular so as to create physical attachment points or locations to assist with retention of the microparticle into or onto a substrate such as, but not limited to, a fabric, a textile, fibers, foams or the like, onto which the microparticle is applied. The surface of the microparticle or parts thereof may be irregular, discontinuous and/or rough. The surface of a microparticle or parts thereof may also be regular, continuous and/or smooth.

Due to the methods used to create microparticles, which may include such techniques as homogenization, sonication and planetary centrifugal mixers, the shape of microparticles may vary. While the general shape of microparticles can be controlled such as, but not limited to, through using the vibrational nozzle technique, it should be appreciated that for convenience microparticles are categorized and grouped by their size rather than by their shape.

In a specific, but non-limiting, example of implementation, the microparticles have all three dimensions in the range of about 0.1 µm to about 200 µm, preferably in the range of about 1 µm to about 50 µm and most preferably in the range of about 2 µm to about 20 µm. Preferably, all three dimensions of the microparticles permit dispersion of an active ingredient within the microparticles and allow retention of the microparticles in the substrate onto which the microparticles are applied, such as for example, in the interstices, pores or cross linkage openings in a substrate, or onto the substrate itself (e.g., onto the fibers of a textile) or absorbed into the substrate (e.g., absorbed into the fibers of a textile).

As used herein, the term "size" refers to the largest dimension of the microparticle.

In a further specific, but non-limiting example, the microparticles have a size that permits the incorporation of one or more nanoparticles having an active ingredient dispersed therein. Nanoparticles generally include small particles with all three dimensions less than 100 nanometers. Nanoparticles also include subcategories such as nanopowders, nanoclusters and nanocrystals. Nanocluster generally refers to an amorphous/semicrystalline nanostructure with at least one dimension being between about 1 nm and about 10 nm and a narrow size distribution. Nanopowder generally refers to an agglomeration of noncrystalline nanostructural subunits with at least one dimension less than 100 nm. Nanocrystal generally refers to any nanomaterial with at least one dimension ≥100 nm and that is single crystalline.

Microparticles may be visualized using techniques such as, but not limited to, extraction method with tracer techniques (e.g., electron microscopy). Other techniques to visualize microparticles will be known to those of skill in the art. The size of the microparticle is determined by techniques well known in the art, such as, but not limited to, photon correlation spectroscopy, laser diffractometry, scanning electron microscopy and/or 3CCD (charged-couple device).

Visual indicators may also be added to the microparticles to promote their visualization. For example, the microparticles may incorporate a labeled dye into or onto the microparticles. Variants of labeled microparticles include additional dyes and/or bioreactive substances.

Microparticles may be electrostatically charged or may be electrostatically uncharged. In particular, the surface of the microparticles may have a residual positive charge or a residual negative charge. Methods to assess surface charges of a microparticle will be apparent to the skilled workers in the art.

Microparticles may be obtained from a formulation comprising a carrier material, wherein the carrier material may be hydrophilic or hydrophobic. As intended by the present specification, the formulation represents the milieu from which the microparticles are formed and/or the environment of the formed microparticles. A formulation may or may not comprise microparticles dispersed therein.

As used herein, the term "hydrophilic" or "hydrophile" refers to a physical property of a molecule that can transiently bond with water through hydrogen bonding. A hydrophilic molecule or portion of a molecule is one that is typically charge-polarized and capable of hydrogen bonding, enabling it to dissolve more readily in water than in oil or other hydrophobic solvents.

The term "hydrophobe" or "hydrophobic" refers to the physical property of a molecule that is repelled from a mass of water. Hydrophobic molecules tend to be non-polar and thus prefer other neutral molecules and non-polar solvents. Examples of hydrophobic molecules include alkanes, oils, fats, and greasy substances in general.

In a specific, but non-limiting implementation of the present invention, the carrier material includes lipids, fatty acid-based lipids, glycerides, fatty acids, paraffin, waxes, or any combination thereof.

Lipids generally include any fat-soluble (lipophilic), naturally-occurring molecules, such as, but not limited to, fats, oils, waxes, cholesterol, sterols, fat-soluble vitamins (such as vitamins A, D, E and K), monoglycerides, diglycerides, phospholipids, and others. Other types of lipids that may be suitable carrier material will be readily recognized by skilled workers in the art.

As used herein, the term "fatty acid" or "fatty acid moiety" includes aliphatic monocarboxylic acids, derived from, or contained in esterified form in an animal or vegetable fat, oil, wax or the like. Natural fatty acids commonly have a chain of 4 to 28 carbons. The fatty acid moiety may be saturated or unsaturated, linear or branched and may be such as, but not limited to, caproic acid, caprylic acid, capric acid, undecanoic acid, lauric acid, tridecanoic acid, myristic acid, pentadecanoic acid, palmitic acid, heptadecanoic acid, stearic acid, oleic acid, elaidic acid, linoleic acid, linolenic acid, arachidic acid, and arachidonic acid, or a fatty acid derivative such as an aryl-fatty acid derivative (e.g., phenylacetyl) or a cycloalkyl-fatty acid derivative (e.g., cyclohexylacetyl or cyclohexylpropionyl), arylacyl moieties include, but are not limited to, benzoyl. A person skilled in the art would readily recognize a fatty acid or a fatty acid moiety.

Fatty acid-containing lipid includes lipids which comprise fatty acid moieties. Glycerides or acylglycerols include esters formed from glycerol and fatty acids.

In one specific, but non-limiting example, the carrier material is glycerol monostearate, tristearin (tristearic acid), tripalmitin (a triglyceride of palmitic acid), stearic acid, palmitic acid, mysitic acid, lauric acid, parafin, bee's wax or any combination thereof.

Table 1 shows examples of carrier materials that may be used as components of the formulation, the proportion in which these carrier materials may be used and the expected melting temperature of each carrier material;

TABLE 1

Examples of carrier material that may be used in the formulations defined herein

| Carrier material | KAR | GSM | TS | TP | SA | PA | MA | LA | Melting temp (° C.) |
|---|---|---|---|---|---|---|---|---|---|
| Shea butter (KAR) | 100 | | | | | | | | 32 |

TABLE 1-continued

Examples of carrier material that may be used in the formulations defined herein

| Carrier material | KAR | GSM | TS | TP | SA | PA | MA | LA | Melting temp (° C.) |
|---|---|---|---|---|---|---|---|---|---|
| Glycerol monostearate (GMS) | | 100 | | | | | | | 62 |
| Tristearin (TS) | | | 100 | | | | | | 60 |
| Tripalmitin (TP) | | | | 100 | | | | | 61 |
| Stearic acid (SA) | | | | | 100 | | | | 56 |
| Palmitic acid (PA) | | | | | | 100 | | | 62 |
| Myristic acid (MA) | | | | | | | 100 | | 53 |
| Lauric acid (LA) | | | | | | | | 100 | 44 |
| SAPA | | | | | 65 | 35 | | | 48 |
| TSGMS | | 39 | 61 | | | | | | 50 |
| TSGMS | | 21 | 79 | | | | | | 50 |
| TPGMS | | 41 | | 59 | | | | | 45 |
| LASA | | | | | 25 | | | 75 | 32 |
| MASA | | | | | 31 | | 69 | | 43 |
| TPSAGMS | | 20 | | 59 | 21 | | | | 46 |
| TSSAGMS | | 20 | 58 | | 22 | | | | 47 |
| LAGMS | | 51 | | | | | | 49 | 39 |
| LAMASA | | | | | 29 | | 49 | 22 | 33 |
| TPMAGMS | | 19 | | 51 | | | 30 | | 41 |
| LASAGMS | | 21 | | | 19 | | | 60 | 32 |
| MASAGMS | | 20 | | | 23 | | 57 | | 40 |
| LASA | | | | | 29 | | | 71 | 33 |
| LATS | | | 32 | | | | | 68 | 33 |
| LASAKAR | 13 | | | | 26 | | | 61 | 31 |
| TPMAGMS | | 25 | | 62 | | | 13 | | 44 |

The formulations may further comprise a surfactant, a binding agent, an active ingredient, or any combination thereof.

A surfactant may be used in the instant formulations to disperse the carrier material into water and to confer a residual charge to the microparticles. The surfactant may be cationic (based on quaternary ammonium cations), anionic (based on sulfate, sulfonate or carboxylate anions), nonionic or amphoteric. Examples of surfactant are, but are not limited to, sodium dodecyl sulfate (SDS) and other alkyl sulfate salts, sodium laureth sulfate, also known as sodium lauryl ether sulfate (SLES), alkyl benzene sulfonate, soaps, fatty acid salts, cetyl trimethylammonium bromide (CTAB), cetyl trimethylammonium chloride (CTAC) and other alkyltrimethylammonium salts, cetylpyridinium chloride (CPC), polyethoxylated tallow amine (POEA), benzalkonium chloride (BAC), benzethonium chloride (BZT), zwitterionic (amphoteric), dodecyl betaine, dodecyl dimethylamine oxide, cocamidopropyl betaine, coco ampho glycinate, nonionic alkyl poly(ethylene oxide), copolymers of poly(ethylene oxide) and poly(propylene oxide) (commercially called Poloxamers, Pluronics or Poloxamines), alkyl polyglucosides, including: octyl glucoside, decyl maltoside, fatty alcohols, cetyl alcohol, oleyl alcohol, cocamide MEA, cocamide DEA, sorbitol ester or fatty acids, or any combination thereof.

Sucrose esters may also be used as surfactant. Sucrose esters suitable for use in the present invention have been used for other purposes such as biologically decomposable emulsifiers in food processing, in the pharmaceutical industry, in cosmetics and in household detergent formulations. Sucrose esters consist largely of the sucrose mono- and di-esters of the natural fatty acids having 12 to 20 carbon atoms and preferably 16 to 20 carbon atoms. The sucrose esters that may used in the present invention include sucrose cocoate, sucrose dilaurate, sucrose distearate, sucrose laurate, sucrose myristate, sucrose oleate, sucrose palmitate, sucrose polylaurate, sucrose polylinoleate, sucrose polyoleate, sucrose polystearate, sucrose stearate, sucrose tetrastearate, sucrose tribehenate, sucrose tristearate or any combination thereof.

A binding agent may be used in the instant formulations to confer stability to the formulations. Binding agents that may be useful in the present invention include, but are not limited to, polyacrylics (also referred herein as PAC), polyurethanes (also referred herein as PU), polysiloxanes (also referred herein as POL), polyvinylpyrrolidone (also referred herein as PVP), guar gum, resin or acrylic base or any combination thereof. Other binding agents that are useful elements in the formulations defined herein will be apparent to a person skilled in the art.

In a specific, but non-limiting implementation of the present invention, the formulation may comprise any combination of the elements listed in Table 2:

TABLE 2

Examples of elements that may be used in the formulations defined herein

| Name | Abbreviations used herein | Function |
|---|---|---|
| Glycerol monostearate | GMS | carrier material |
| Tristearin | TS | carrier material |

TABLE 2-continued

Examples of elements that may be used in the formulations defined herein

| Name | Abbreviations used herein | Function |
|---|---|---|
| Tripalmitin | TP | carrier material |
| Stearic acid | SA | carrier material |
| Palmitic acid | PA | carrier material |
| Mysitic acid | MA | carrier material |
| Lauric acid | LA | carrier material |
| Paraffin | PARA | carrier material |
| Bee's wax | BEE | carrier material |
| Shea butter | KAR | carrier material/active ingredient |
| Cetyl trimethylammonium chloride | CTAC | surfactant |
| Sodium laureth sulfate | ESB | surfactant |
| PolyAc M-4445 | PAC | binding agent |
| PU30 | PU | binding agent |
| Polon | POL | binding agent |
| PVP K90 | PVP | binding agent |

In a further specific, but non-limiting implementation, the formulation may comprise any of the following combination of elements:

LA+SA; also referred herein as LASA;
SA+PA; also referred herein as SAPA;
LA+SA+PAC; also referred herein as LASA/PAC;
LA+SA+KAR; also referred herein as LASAKAR;
LA+SA+KAR+PAC; also referred herein as LASAKAR/PAC;
TS+MA+GMS; also referred herein as TPMAGMS;
TS+MA+GMS+PAC; also referred herein as TPMAGMS/PAC.

In a further specific but not limiting implementation, the formulation may comprise a natural butter, such as, shea butter, lemon butter, cocoa butter, grape seed butter, mago butter, sal butter, Illipe butter, kokum butter, pentadesma butter or the like, or any combination thereof. The natural butter may also be used as carrier and/or as an active ingredient in the formulations defined herein.

Microparticles may also be obtained from formulations that comprise natural butters and the microparticles obtained from such formulation also comprise natural butters. In such embodiment, the microparticles comprise about 25% to about 40% of natural butters, more preferably about 30 to about 35% of natural butters.

In a further specific, but non-limiting implementation, the microparticles melt at a temperature between about 20° C. to about 60° C.

In a further specific but non-limiting example, the pH of the formulation may be in the range of from about 4 to about 10; preferably in the range of from about 6 to about 8.

A person skilled in the art will appreciate that other elements and other proportions may be used in the formulations without departing from the desired utility of the formulations defined herein.

II. Methods for the Manufacture of Formulations Comprising Microparticles

Generally, in the method of manufacturing a formulation comprising the microparticles, the first step includes the selection of the elements for preparing the formulation. For example, such selection includes; 1) selecting one or more carrier material; 2) selecting one or more active ingredient; 3) selecting one or more surfactant; and 4) selecting one or more binding agent. The selected carrier materials and selected active ingredient(s) are mixed and melted so as to form a liquid phase that is mixed in an aqueous solution of the surfactant that may be pre-heated and homogenized to obtain microdoplets. The molten liquid or stirred melt comprising the carrier materials and the active ingredient may be dispersed into microdroplets using techniques such as, but not limited to, stirring or sonication. Upon cooling, the microdoplets solidify into microparticles. The binding agent is added and mixed to the dispersion to form the formulation containing the microparticles. Any variation in this general method which results in the formation of formulations comprising microparticles is also encompassed by the present application.

The amounts and ratios of elements composing the formulation; the temperature at which the elements are melted; the speed, frequency and duration of the homogenization step; the temperature at which the formulation is cooled; are all factors that may affect the composition, concentration, size and resistance of microparticles.

The elements of the formulation have low toxicity and are preferably compatible with the active ingredient to be incorporated in the formulation. Preferably, the elements of the formulation should not affect the desirable properties of the active ingredients.

III. Active Ingredient

In a further specific, but non-limiting aspect of the present invention, the microparticles defined herein comprise one or more active ingredient dispersed therein. The active ingredient includes any substance that manifests a desirable property, activity, purpose and/or virtue on, for example a subject or on an object. As used herein, the term "subject" includes humans and animals.

The choice of active ingredient is determined by the desired effect or the desired property to be manifested. Active ingredients include, but are not limited to pharmaceutical agents, therapeutic agents, medicinal agents, nutraceutical agents, cosmetic agents, cleansing agents, detoxification agents, aromatic agents, flavorings agents, surface-active compositions, beautifying agent, etc. The active ingredient may be a naturally-occurring or a synthetic molecule.

Pharmaceutical active ingredients include agents having a direct or indirect beneficial effect upon introduction into or administration to a host. The expression pharmaceutical active ingredient is also meant to indicate prodrug forms thereof. A prodrug form of a pharmaceutical active ingredient means a structurally related compound or derivative of the pharmaceutical active ingredient which, when introduced into or administered to a host is converted into the desired pharmaceutical active ingredient.

Representative examples of pharmaceutical agents include, but are not limited to: antidiarrhoeals, antihypertensives, calcium channel blockers, antiarrhyrthmics, anti-angina agents, beta-adrenergic blocking agents; cardiotonic glycosides, adrenergic stimulants, vasodilators, antimigraine preparations, anticoagulants and thrombolytic agents, hemostatic agents, analgesics and antipyretics, neurotoxins, hypnotics and sedatives, antianxiety agents, neuroleptic and antipsychotic drugs, antidepressants, CNS stimulants, anti-alzheimer's agents, anti-Parkinson's agents, anticonvulsants, antiemetics and antinauseants, non-steroidal anti-inflammatory agents, antirheumatoid agents, muscle relaxants, agents used in gout and hyperuricaernia, oestrogens, progesterone and other progestagens, antiandrogens, antioestrogens, androgens and anabolic agents, corticosteroids, pituitary hormones and their active derivatives or analogs, hypoglycemic agents, thyroid hormones, other miscellaneous hormone agents, pituitary inhibitors, ovulation inducers, diuretics, antidiuretics, obstetric drugs, prostaglandins, antimicrobials, penicillins, tetracyclines, aminoglycosides, antifungals, quinolones, sulphonamides, sulphones, other miscellaneous antibiotics, antituberculosis drugs, antimalarials, antiviral agents, anthelmintics, cytotoxic agents, weight reducing agents, agents used in hypercalcaemia, antitussives, expectorants, decongestants, bronchospasm relaxants, antihistamines, local or topical anaesthetics, stratum corneum lipids, ceramides, cholesterol and free fatty acids, neuromuscular blocking agents, smoking cessation agents, insecticides and other pesticides which are suitable for local or topical application, dermatological agents, allergens for desensitisation, nutritional agents or keratolytics.

A therapeutic agent include agents that are effective to ameliorate symptoms associated with a disease, a disorder or a condition to lessen the severity or cure the disease, disorder or condition or to prevent the disease, disorder or condition from occurring. The term treatment refers to both therapeutic treatments as well as to prophylactic and preventative measures.

Representative examples of therapeutical agents include, but are not limited to: acepromazine, acetaminophen, acetohexamide, acetohydroxamic acid, acetylcholine, acetylcysteine acyclovir, albendazole, alclometasone dipropionate, allopurinol, alprazolam, alprostadil, amcinoide, amantadine, amidinocillin, amikacin amiloride, aminocaproic acid, aminophylline, aminosalicylate, aminosalicylic acid, amitriptyline hydrochloride, ammonium chloride, amobarbital, amodiaquine hydrochloride, amoxapine, amoxicillin, amphetamine sulfate, amphotericin, ampicillin amprolium, acetazolamide acetyldigoxin, acetylsalicylic acid, anileridine, anthralin, antipyrine, antivenin, apomorphine, apraclonidine, ascorbic acid, aspirin, acromycin atropine, amoxycillin anipamil, azaperone azatadine maleate, azathioprine, azithromycin, aztreonam, bacampicillin, bacitracin, baclofen, barium salts, beclomethasone diproionate, belladonna extract, bendroflumethiazide, benoxinate hydrochloride, benzethonium chloride, benzocaine, benzonatate benzthiazide, benztropine mesylate, betaine, betamethasone, betaxolol, betanechol chloride, biotin, biperiden, bisacodyl, bismuth, botulism antitoxin, bromocriptine mesylate, bromodiphenhydramine hydrochloride, bumetanide, bupivacaine, busulfan butabarbital sodium, butalbital, combinations of butalbital, caffeine and aspirin and codeine, beta-carotene, calcifediol, calcium carbonate, calcium citrate, calcium salts, candicidin, captopril, carbachol, carbamazepine, carbenicillin indanyl sodium, carbidopa, carbinoxamine maleate, carboprost tromethamine, carboxymethyl cellulose, carisoprodol, casanthranol, cascara, castor oil, cefaclor, cefadroxil, cefamandole nafate, cefazolin, cefixime, cefoperazone, cefotaxime, cefprozil, ceftazidime, cefuroxime axetil, cephalexin, cephradine, ceramic powder, chlorambucil, chloramphenicol, chlordiazepoxide, chloroquine phosphate, chlormadinone acetate, chlorothiazide, chlorpheniramine maleate, chloroxylenol, chlorpromazin, chlorpropamide, chlorprothixene, chlorprothixene, chlortetracycline bisulfate, chlortetracycline hydrochloride, chlorthalidone, chlorzoxazone, cholecalciferol, cholera vaccine, chromic chloride, chymotrypsin, cimetidine, cinoxazin, cinoxate, ciprofloxacin, cisplatin, clarithromycin, clavulanate potassium, clemastine fumarate, clidinium bromide, clindamycin hydrochloride, palmitate and phosphate, clioquinol, clofazimine, clofibrate, clomiphene citrate, clonazepam, cinnarizine, clonidine hydrochloride, clorsulon, clotrimazole, cloxacillin sodium, cyanocobalamin, cocaine, coccidioidin, cod liver oil, codeine, colchicine, colestipol, corticotropin, corisone acetate, cyclacillin, cyclizine hydrochloride, cyclobenzaprine hydrochloride, cyclophosphamide, cycloserine, cyclosporine, cyproheptadine hydrochloride, cysteine hydrochloride, danazol, dapsone, dehydrocholic acid, demeclocycline, desipramine, desoximetasone, desoxycorticosterone acetate, dexamethasone, dexchlorpheniramine maleate, dexpanthenol, dextroamphetamine, dextromethorphan, diazepam, diazoxide, dibucaine, diclofenac epolamine, dichlorphenamide, dicloxacillin sodium, dicyclomine, dienestrol, diethylpropion hydrochlorid, diethylstilbestrol, diflunisal, digitalis, dicoumarol, digitoxin, digoxin, dihydroergotamine, dihydrostreptomycin, dihydrotachysterol, dihydroxyaluminium amino acetate, dihydroxyaluminium sodium carbonate, diltiazem hydrochloride, dimenhydrinate, dimercaprol, diphenhydramine hydrochloride, diphenoxylate hydrochloride, diphteria antitoxin, dipyridamole, disopyramide phosphate, disulfuram, dobutamine hydrochloride, docusate calcium, docusate sodium, dopamine hydrochloride, doxepin hydrochloride, doxycycline, doxycycline hyclate, doxylamine cuccinate, dronabinol, droperidol, drotaverine, dydrogesterone, dyphylline, guaifenesin, enalapril maleate, analaprilat, ephedrine, epinephrine, equilin, ergocalciferol, ergoloid mesylates, ergonovine maleate, ergotamine tartrate, erythrityl tetranitrate, erythromycin, estradiol, estriol, estrogene, estrone, estropipate, ethcrynic acid, ethambutol hydrochloride, ethchlorvynol, ethinyl estradiol, ethionamide, ethopropazine hydrochloride, ethotoin, ethynodiol diacetate, etidronate disodium, etoposide, eugenol, famotidine, fentanyl, fenoprofen, ferrous fumatate, ferrous gluconate, ferrous sulfate, flucytosine, fludrocortisone acetate, flunisolide, fluocinolone acetonide, fluocinonide, fluorescein sodium, fluorometolone, fluorouracil, fluoxymesterone, fluphenazine, flurandrenolide, flurazpam, flurbiprofen, folic acid, furazolidone, flunitrazepam, furosemide, gemfibrozil, gentamicin, gentian violet, glutarate, glutethimide, glycopyrrolate, chorionic gonadotropin, gramicidin, griseofulvin, guaifenesin, guanabenz, guanadrelsulfate, halazone, haloperidol, haloprogin, halothane, heparin calcium, hepatitis virus vaccine, hetacillin potassium, hexylresorcinol, histamine phosphate, histidine, homatropine, histoplasmin, hydralazine hydrochloride, hydrochlorothiazide, hydrocodone bitartrate, hydrocortisone, hexobarbital, hydroflumethiazide, hydromorphone hydrochloride, hydroquinone, hydroxocobalamin, hydroxyamphetamine, hydroxychloroquine sulfate, hydroxyprogesterone caproate, hydroxyurea, hydroxine hydrochloride, hydroxine pamoate, hyoscyamine, hyoscyamine sulfate, ibuprofen, ifosfamide, imipramide, imipramide hydrochloride, indapamide, indomethacin, insulin, inulin, ocetamid, iodoquinol, iohexyl, iopamidol, ipecac, ipodate calcium, ipodate sodium, isocarboxacid, isoetharine hydrochloride, isoflurane, isoniacid, isopropamide iodine, isoproterenol hydrochloride, isosorbide dinitrate, isotretenoin, isoxsuprine hydrochloride, kanamycin sulfate, ketoprofen, ketoconazole, labetalol hydrochloride, lanolin, leucine, leucovorin calcium, levamisole hydrochloride, levocamithine, levodopa, levonorgestrel, levorphanol tartrate, levothyroxine sodium, lidocaine, lincomycin hydrochloride, lindane, liothyronine sodium, liotrix, lisinopril, lithium carbonate, loperamide hydrochloride, loracarbef, lonetil, lorazepam, lovastatin, loxapine, lysine, mafenide acetate, magaldrte, magnesium carbonate, magnesiumchloride, magnesium gluconate, magnesium oxide, other magnesium salts, malathinon, manganese salts, manganese, maprotiline hydrochloride, mazindol, measle virus vaccine, mebendazole, mebrofenin, mecamylamine hydrochloride, meclizine hydrochloride, meclocycline, meclofenamate sodium, medroxyprogesterone acetate, mefenamic acid, megestrol acetate, meglumine, melphalan, menadiol sodium diphosphate, menadione, menotropine, meperidine, mephenyloin, mephobarbital, meprednisone, meprobaamate, mercaptopurine, mesoridazine besylate, mestranol, metaproterenol sulfate, metaraminol bitartrate, methacycline hydrochloride, methadone hydrochloride, methamphetamine hydrochloride, methazolamide, methdilazine, methenamine, methicillin sodium, methimazole, methionine, methocarbamol, methotrexate, methoxsalen, methoxyflurane, methsuximide, methyclothiazide, methylbenzethonium chloride, methyldopa, methylergonovine maleate, methylphenidate hydrochloride, methylprednisolone, methyltestosterone, methysergide maleate, metoclopramide, metolazone, meoprolol tartrate, metronidazole, metyrapone, metyrosine, mexiletine hydrochloride, mexiletine hydrochloride, miconazole, minocycline hydrochloride, minoxidil, mitomycin, mitotane, molindone hydrochloride, monobenzone, morphine sulfate, mupirocin, medazepam, mefruside, methandrostenolone, methylsulfadiazine, nadolol, nafcillin, nafcillin sodium, nalidixic acid, nalorphine, naloxone, nandrolone decanoate, nandrolone phenpropionate, naproxen, natamycin, neomycin, neomycin sulfate, neostimine bromide, niacin, nitrofurantoin, nalidixic acid, nifedipine, nitrazepam, nitrofurantoin, nitroglycerine, nitromerson, nizatidine, nonoxynol-9, norethindrone, norethindrone acetate, norfloxacin, norgestrel, nortriptyline hydrochloride, noscapine, novobiocin sodium, nystatin, opium, oxacillin sodium, oxamniquine, oxandrolone, oxazepam, oxprenolol hydrochloride, oxtriphylline, oxybenzone, oxybutynin chloride, oxycodone hydrochloride, oxycodone, oxymetazoline hydrochloride, oxymetholone, oxymorphone hydrochloride, oxyphenbutazone, oxytetracycline, padimate, panreatin, pancrelipase, papain, panthenol, papaverin hydrochloride, parachlorophenol, paramethasone acetate, paregoric, paromomycin sulfate, penicillamine, penicillin, penicillin derivatives, pentaerythritol tetranitrate, pentazocine, pentazocine hydrochloride, pentazocine salts, pentobarbital sodium, perphenazine, pertussis, phenacemide, phenazopyridine hydrochloride, phendimetrazine tartrate, phenelzine sulfate, phenmetrazine hydrochloride, phenobarbital, phenophtalein, phenoxybenzamine hydrochloride, phentermine hydrochloride, phenylalanine, phenylbutazone, phenylephrine hydrochloride, phenylpropanolamine hydrochloride, physostigmine, phytonadione, pilocarpine, pimozide, pindolol, piperazine, piroxicam plicamycin, poliovirus vaccine inactivated, polycarbophil, polymycin b sulfate, polythiazide, potassium chloride, potassium citrate, potassium cluconate, potassium iodine, potassium sodium tartrate, povidone iodine, pralidoxime chloride, pramoxine hydrochloride, pramezam, prazepam, praziquantel, prazosin hydrochloride, prazosin hydrochloride, prednisolone, prilocaine, primaquine, primidone, probenecid, probucol, procainamide hydrochlorid, procaine hydrochloride, procarbacine hydrochloride, prochlorperazine, prochlorperazine maleate, procyclidine hydrochloride, progesterone, proline, promazine, promazine hydrochloride, promazine, promethazine, promethazine hydrochloride, propafenone hydrochloride, propantheline, proparacaine hydrochloride, propoxycaine hydrochloride, propoxyphene hydrochloride, propoxyphene napsylate, propanolol hydrochloride, propyliodone, propylthiouracil, propylthiouracil, protriptyline hydrochloride, pseudoephedrine hydrochloride, pumice, pyrantel pamoate, pyrazinamide, pyrethrum extract, pyridostigmine bromide, pyridoxine hydrochloride, pyrilamine maleate, pyrimethamine, pyroxylin, pyrvinium pamoate, phenacetin, phenyloin, prednisone, uinidine gluconate, quinidine sulfate, rabies vaccine, racepinephrine ranitidine, rauwolfia serpentina, resorcinol, ribavirin, riboflavin, rifampin, ritodrine, rubella virus vaccine, saccharin, saccharin sodium, salicylamide, salicylic acid, salsalata, scopolamine, secobarbital sodium, selenius acid, selenium sulfate, sennaserine, simethicone, sodium ascorbate, sodium bicarbonate, sodium fluoride, sodium gluconate, sodium iodide, sodium lactate, sodium nitrite, sodium ditroprusside, sodium salicylate, spironolactone, stannozolol, streptomycin, sucralfate, sulfacetamide, sulfadiazine, reserpine, sulfadioxine, sulfamerazine, sulfamethazine, sulfamethizole, sulfamethoxazole, sulfamethoxydiazine, sulfapyridin, sulfasalazine, sulfaperin, sulfathiazole, sulfisoxazole, sulfinpyrazone, sulindac, suprofen, stilains, tamoxifen citrate, taurine, temacepam, terbutaline sulfate, terfenadine, terpin, testolacton, testosterone, tolazamide, tolbutamide, tetracaine, tetracycline, tetrahydrocycline, theophylline, thiabendazole, thiamine hydrochloride, thiamin, thiamylal, thiethylperazine thimerosal, thioguanine, thioridazine hydrochloride, thistrepton, thiotepa, thiothixene, threonine, thyroid, ticarcillin, timolol, tioconazole, titaniumdioxide, tutanium powder, tolazamide, tolbutamide, tolmetin, tolnaftate, trazodone hydrochloride, tretinoin, triacetin, triamcinolone, triamterene, triazolarn, trichorfon, trichlonnethiazide, trientine hydrochloride, trifluoperazine hydrochloride, triflupromazine, trihexyphenidyl hydrochloride, trimeprazine tartrate, trimethadione, trimethobenzamide hydrochloride, trimethoprim, trioxsalen, tripelennamine, triprolidine, trisulfapyrimidine, tropicamide, trypsin, tryptohan, tuberculin, tyloxapol, tyropanoate sodium, tyrosine, tyrothricin, thyrothricin bethamethasone, thiotic acid, sotalol, salbutamol, norfenefrine, silymarin, dihydroergotamine, buflomedil, etofibrate, indometacin, urea, valine, valproic acid, vancomycin hydrochloride, vasopressin, verapramil, vidarabine, vinblastine, vincristine, vitamins, warfarin, yellow fever vaccine, zinc acetate, zinc carbonate, zinc chloride, zinc gluconate, beta acetyl digoxin, piroxicam, haloperidol, ISMN, amitriptylin, diclofenac, nifedipine, verapamil, pyritinol, nitrendipin, doxycycline, bromhexine, methylprdnisolone, clonidine, fenofibrate, allopurinol, pirenyepine, levothyroxin, tamoxifen, metildigoxin, o-(beta-hydroxyethyl)-rutoside, propicillin, aciclovir mononitrate, paracetamol, naftidrofuryl, pentoxifylline, propafenone, acebutolol, L-thyroxin, tramadol, bromocriptine, loperamide, ketotifen, fenoterol, cadobelisate, propanolol, enalaprilhydrogen maleate, bezafebrate, ISDN, gallopamil, xantinol nicotinate, digitoxin, flunitrazepam, bencyclane, dexapanthenol, pindolol, lorazepam, diltiazem, piracetarn, phenoxymethylpenicillin, furosemide, bromazepam, flunarizin, erythromycin, metoclopramide, acemetacin, ranitidin, biperiden, metamizole, doxepin, dipotassium chloroazepate, tetrazepam, estramustine phosphate, terbutaline, captopril, maprotiline, prazosin, atenolol, glibenclamide, cefaclor, etilfrine, cimetidine, theophylline, hydromorphone, ibuprofen, primidone, clobazam, oxaceprol, medroxyprogesterone, flecainid, pyridoxal-5-phosphate glutaminate, hymechromone, etofylline clofibrate, vincamine, cinnarizine, diazepam, ketoprofen, flupentixol, molsimine, glibornuride, dimetinden, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, murtol, bromelaine, prenylamine, salazosulfapyridine, astemizol, sulpiride, benzerazide, dibenzepine, acetylsalicylic acid, miconazol, nystatin, ketoconazole, sodium picosulfate, coltyramine, gemfibrocil, rifampicin, fluocortolone, mexiletin, amoxicillin, terfenadrin, mucopolysaccharide polysulfade, triazolam, mianserin, tiaprofenic acid, amezinium metilsulfate, mefloquine, probucol, quinidine, carbamazepine, L-aspartate, penbutolol, piretanide, aescin amitriptyline, cyproterone, sodium valproinate, mebeverine, bisacodyl, 5-aminosalicylic acid, dihydralazine, magaldrate, phenprocoumon, amantadine, naproxen, carteolol, famotidine, methyldopa, auranofine, estriol, nadolol, levomepromazine, doxorubicin, medofenoxate, azathioprine, flutamide, norfloxacin, fendiline, prajmalium bitartrate, lipid derivatives of phosphonatides, amphiphilic polymers, adenosine derivatives, sulfated tannins, monoclonal antibodies, and metal complexes of water soluble texathyrin.

Representative nutraceutical agents include components which promote or prevent disease or enhance well-being such as antioxidants, phytochemicals, hormones, vitamins such as Vitamin C and Vitamin E, pro-vitamins, minerals, microorganisms such as bacteria, fungi and yeast, prebiotics, trace elements, essential and/or highly unsaturated fatty acids such as omega-3 fatty acids and mid-chain triglycerides, nutritional supplements, enzymes, pigments, oligopeptides, dipeptides and amino acids.

The active ingredient may also be a protein, an enzyme, a peptide, a polysaccharide, a nucleic acid, a cell fragment, a biologically active substance, a salt, or the like. The actice agent may also be a lipid such as, but not limited to, fat-soluble vitamins (e.g., vitamins A, D, E and K), ceramides in which the fatty acid components may be one or more of the following: alpha-hydroxy 6-hydroxy-4-sphingenine, alpha-hydroxy phytosphingosine, alpha-hydroxy sphingosine, ester linked omega-hydroxy 6-hydroxy-4-sphingenine, non-hydroxy phytosphingosine, non-hydroxy sphingosine, and/or ester linked omega-hydroxysphingosine and free sterols.

The active ingredients may have cosmetic properties such as, but not limited to: moisturizing and/or humectant, dermatological, self-tanning, anti-allergenic, anti-hair re-growth, anti-acne and/or seboregulator, anti-ageing, anti-dandruff, antimicrobial, antioxidant, antiperspirant/deo-active, antipuffing, antistatic, anti-stretch marks, anti-tartar, anti-wrinkle, astringent, conditioning, cooling, complexing and sequestering, depilatory, depigmentors, draining, dyes, emollient, exfoliating, firming/botox-like, foaming, hair growth, healing, heating, insects repellents, lightening/whitening, myorelaxing, natural sun protector, nourishing, protective, perfumes, pearlescent agents, plant extracts, purifying, radiance, rebalance, refreshing, regenerating/revitalizing, repairing, restructuring/replenishing, softener, shining, slimming, smoothing, soothing, tensing, toning/invigorating, venotonic, vitamins etc.

The active ingredient may also counteract cellulite, counteract the loss of hair, decrease fat deposition, treat discoloring of the skin, modify aspects of a body part, muscle toner, skin or hair, may prevent cavities, prevent or treat dental plaque, prevent redness/anti-rosacea, or the like.

Non-limiting examples of cosmetic agent include: glycerin, lactic acid and/or lactates, sodium lactate, butylene glycol, propylene glycol, biosaccaride gum-1, glycine soy, ethylhexyloxyglycerin, pyrrrolidone, carboxylic acid, hyaluronic acid, chitosan, fucose-rich polysaccharide, vitamins A, $B_{1-6}$, $B_{12}$, C, D, E, F, H, K, and PP, as well as their derivatives, retinyl palmitate, ascorbyl glucoside, tocopheryl acetate, tocopheryl palmitate, niacinamide, panthenol, alpha-lipoic acid, phytoene, D-biotin, coenzyme Q10, alpha-glucosylrutin, carnitine, carnosine, natural and/or synthetic isoflavonoids, creatine, creatinine, lignans, taurine, and/or b-alanine, panthenol, allantoin, tannin, and plant active ingredients, such as azulene and bisabolol, glycyrrhizin, hamamelin and plant extracts, such as camomile, aloe vera, hamamelis, and liquorice.

The formulation may also comprise irritation-mitigating additives to minimize or eliminate the possibility of skin irritation or skin damage resulting from the active ingredient or other components of the formulation. Suitable irritation-mitigating additives include, for example: alpha-tocopherol; monoamine oxidase inhibitors, particularly phenyl alcohols such as 2-phenyl-1-ethanol, glycerin, salicylic acids and salicylates, ascorbic acids and ascorbates, ionophores such as monensin, amphiphilic amines, ammonium chloride, N-acetylcysteine, cis-urocanic acid, capsaicin, and chloroquine.

In a specific, but non-limiting example, the active ingredient may have deodorizing properties and/or scents such as deodorants, fragrances or perfumes that are used to mask odor S or replace an unwanted odor with a more desired one. As used herein, deodorizing agents include agents that capture and remove smells from the surrounding air or object or skin. Representative examples of the deodorizing agents include pine oil, activated charcoal and aqueous solutions containing chlorine, glyoxal, glycol, zeolite, silica, quartz diorite-porphyrite, and/or calcium chloride. The deodorizing agent may be used to remove one or more unwanted smells from an area, such as those of human sweat caused by odor-causing microbes on the skin, hydrogen sulfide, animal hair and dander, cigarette smoke.

A fragrance include aqueous solutions made from, but not limited to, the following ingredients or combinations thereof: aromatic compounds made from fragrant essential oils, such as those made from plants like rose, jasmine, lavender; fruits, such as oranges, lemons and limes; leaves, such as sage and rosemary; seeds, such as the cocoa bean, coriander seed, cardamom seed and anise seed; woods, such as those from pine, fir, and sandalwood trees; seaweed; lichens or moss, or the like. The fragrance is generally used to give the surrounding air or selected objects a particular desired smell that can be used to mask other odors or scents or add to the surrounding area a desirable scent. In some implementations, the active ingredient may be a combination of a deodorizing agent and a fragrance.

In a further, but non-limiting example, the active ingredient may also be suitable for the reduction and potential blocking of UV rays to exposed skin. As used herein, a sunscreen (also referred to as sun block) include topically applied compound that reduces or reflects (blocks) certain wavelengths of the ultraviolet (UV) spectrum in sunlight, specifically UV-A rays in the 400 nm to 315 nm spectrum and UV-B rays in the 315 nm to 280 nm spectrum. Long-term exposure (which varies with the strength of sunlight) to these wavelengths may cause sunburn and may also contribute to the onset and development of certain serious conditions and types of cancer, most notably the skin cancer melanoma.

Representative examples of agents in sunscreen include p-aminobenzoic acid (PABA), padimate O-phenylbenzimidazole sulfonic acid, cinoxate, dioxybenzone, oxybenzone homosalate, methyl anthranilate, octocrylene, octyl methoxycinnamate, octyl salicylate, sulisobenzone, trolamine salicylate, avobenzone, ecamsule, titanium dioxide, and zinc oxide.

Representative agents that may treat the effects of sunburn typically include cream or gel solution of aloe vera, vitamin E, and hydrocortisone. Another variant on the above method for using the active ingredient may also conceivably deliver agents that tint the skin with a particular shade, color or hue that mimics the effect of exposure to the sun (this is commonly referred to as a "sunless tan"). Representative agents that may deliver a "sunless tan" include dihydroxyacetone (DHA), erythrulose, and canthaxanthin.

Active ingredients may also have cleansing or detoxifying properties. Representative examples of such active ingredients include disinfectants such as chlorohexidine gluconate, cetramide, benzylknium chloride or peptides such as polymixin B.

In specific, but non-limiting examples, some active ingredients may be used to achieved the following results: shea butter may be used to hydrate or heal the skin; caffeine may be used to remove fat; mango butter may be used to moisturize skin; green tea may be used to stimulate; vitamin A palmitate may be used as an anti-aging agent or as an anti-oxidant agent; vitamin C palmitate may be used as an anti-ageing agent, an anti-oxidant agent, for whitening the skin; wheat cerasome powder may be used as an anti-aging agent; glycerrhizinic acid may be used as an anti-inflammatory agent, as a calming agent or a revitalizing agent; cococin may be used to improve hair growth, cell growth and blood circulation; ursolic acid may be used to increase collagen levels; venocin may be used to improve blood circulation and scaring; vitacell powder may be used as a tonic or a detoxifying agent. Such agents may also be used in combination such as, for example, venocin or cococin may be combined to caffeine to treat cellulites; venocin, vitacell and minerals may be combined to be used as a toner.

Other active ingredients may include: aluminum trihydrate as a fire retardant, astringent; acediasulfone as a antibacterial; agaricic acid as a antiperspirant; alclometastone as a topical anti-inflammatory; calcium alginate as a topical hemostatic; amidomycin as a fungicide; antimony oxide as a fire retardant; apigenin as a yellow dye, mordant; aspirin as an anti-inflammatory, antipyretic; azanidazole as a antiprotozoal (trichomonas); azelaic acid as a antiacne; baicalein as an astringent; bendazac as an anti-inflammatory; benomyl as a fungicide, ascaricide; benzestrol as estrogen; benzylpenicillinic acid as an antibacterial; benzylsulfamide as an antibacterial; bergaptene as an antipsoriatic; betasine as an iodine source; bezitramide as a narcotic analgesic; bibrocathol as a topical antiseptic; bietanautine as an antihistaminic; bifenox as a herbicide; bifonazole as an antifungal; binapacryl as a fungicide, miticide; bis(p-chlorophenoxy)methane as a miticide; bismuth aluminate as an antacid; bismuth iodide oxide as an anti-infective; bismuth phosphate as an antacid, protectant; bismuth subcarbonate as a topical protectant; bismuth subgallate as an astringent, antacid, protectant; bisphenol A as a fungicide; bitertanol as an agricultural fungicide; bithionol as a topical anti-infective; bromacil as an herbicide; bromadiolone as a rodenticide; bromcresol green as an indicator; bromcresol purple as an indicator; bromethalinlin as a rodenticide; p-bromoacetanilide as an analgesic, antipyretic; 3-bromo-d-camphor as a topical counterirritant; bromophos as an insecticide; bromopropylate as an acaricide; 5-bromosalicyl-hydroxamic acid as an antibacterial (tuberculostatic); 5-Bromosalycilic acid acetate as an analgesic; bromosaligenin as an anti-inflammatory; bromthymol blue as an indicator; broxyquinoline as an antiseptic, disinfectant; bucetin as an analgesic; bumadizon as an analgesic, anti-inflammatory, antipyretic; bupirimate as a fungicide; busulfan as an insect sterilant, antineoplastic; butamben as a topical anesthetic; butrylin as an insecticide; butylated hydroxy anisole as an antioxidant (BHA); butyl paraben as a pharmaceutic aid, food preservative; 4-tert-Butylphenyl salicylate as a light absorber; cacotheline as an indicator; cactinomycin as an atineoplastic; cadmium salycilate as an antiseptic; calamine as a skin protectant; calcium carbonate as an antacid; calcium saccharate as a pharmaceutic aid; calcium tartrate as a preservative, deodorant, antacid; cambendazole as an anthelminthic, candicidin as a topical antifungal; candidin as a topical antifungal; capsaicin as a topical analgesic; captan as a fungicide, bacteriostat; carbadox as an antimicrobial; carbamazepine as an anticonvulsant, analgesic; carbarsone as an antiamebic; carbaryl as a contact insecticide; carbazochrome salycilate as an antihemorrhagic; carbendazim as a fungicide; carbophenothion as a miticide, insecticide; carboquone as an antineoplastic; carisoprodol as a skeletal muscle relaxant; carthamin as a dye; carvacrol as a disinfectant; cephalin as a local hemostatic; chalcomycin as an antibiotic; chartreusin as an antibiotic; chitin as a vulnerary; chloramben as an herbicide; chloramphenacol palmitate as an antimicrobial; chloranil as a fungicide; chlorbetamide as an antiamebic; chlordimeform as an insecticide; chlorfenac as an herbicide; chlorfenethol as an acaricide; chlorhexidine as a topical antibacterial; chloroazodin as an antibacterial, topical anesthetic; chlorophacinone as an anticoagulant rodenticide; p-chlorophenol as an antiseptic; chlorothricin as an antibiotic; chlorotrianisene as estrogen; chloroxylenol as an antiseptic, germicide; chlorphenesin as a topical antifungal; chlorphenesin carbamate as a relaxant (skeletal muscle); chlorphenoxamide as an antiamebic; chlorpropamide as an antidiabetic; chlorpyrifos as an insecticide; chlorquinaldol as a topical antibacterial; chlorsulfuron as an herbicide; chlorothion as an insecticide; chlozoxazone as a relaxant; cholesterol as a pharmaceutic aid; chromic carbonate as a pigment; chromic hydroxide as a pigment; chromic oxide as an abrasive; chromic phosphate as a green pigment; chrysarobin as an antpsoriatic; cilastazol as an antithrombotic; cinoxate as a sunscreen agent; ethylenediaminetetraacetic acid (EDTA) as an odor absorbent; disodium salt of EDTA as a chelator; sodium bicarbonate as an odor absorbent/pH modifier; acarbose as an antidiabetic; acefylline piperazine as a bronchodilator; acenocoumarol, sodium salt as an anticoagulant; acephate as an insecticide; acetaminophen as an analgesic; acetylleucine as an antivertigo agent; monoethanolamine acid Violet 7B as a dye/stain; acitretin as an antipsoriatic; acranil as an antiprotozoal (Giardia); acriflavine as an anti-infective; actaplanins as a growth stimulant; algestone acetophenide as an antiacne; algin as an hemostatic; almagate as an antacid; (−)-ambroxide as a fragrance; ambucaine hydrochloride as a local anesthetic; amodiaquin as an antimalarial; anabasine hydrochloride as an insecticide; o-anisaldehyde as a fragrance; anisomycin hydrochloride as a topical antitrichomonal; aralkonium chloride as an antiseptic, germicide; asiaticoside as a dermatide, wounds, burns; bebeerine as an antimalarial; potassium benzoate as a preservative, antifungal; benzoyl peroxide as a dermatide, antiacne; benzylidene acetone as a fragrance; bidrin as an insecticide; biphenamine hydrochloride as an antiseborrheic; bishydroxycoumarin as an anticoagulant; bismuth tribromophenate as a topical antiseptic; blasticidin S hydrochloride as an antimicrobial; bromocresyl as a green indicator; bromophenol blue as an indicator; butathamine hydrochloride as an anesthetic; calcium ascorbate as Vitamin C/calcium source; calcium bisulfite as a germicide; calcium thioglycollate as a depilatory; carbowax as an ointment base; cetalkonium chloride as an antibacterial; cethoxonium bromide as an antiseptic; chartreusin as an antimycobacterial; chloramine-T as a topical antiseptic; cinnamic acid as a fragrance; cotamine chloride as an hemostatic; demercarium bromide as a topical antiglaucoma; D-2-deoxyribose for DNA synthesis; dequalinium chloride as an antiseptic; dermostatin as an as an indicator of nitrates/nitrites; diamthazole dihydrochloride as an antifungal; dibekacin sulfate as an antibacterial; 3,5-Dibromo-4-hydroxybenzenesulfonic acid sodium salt as a topical disinfectant; dibromopropamidine as a cosmetic preservative; diflorasone as a topical anti-inflammatory; dihydroxyacetone as an artificial tanning agent; diisobutyl sodium sulfosuccinate as a wetting agent/detergent; dimethisoquin as a topical anesthetic; diphenicillin sodium as an antibacterial; diphetarsone as an antiamebic; dipyrone as an analgesic, antipyretic; diquat dibromide as a defoliant; domiphen bromide as a topical anti-infective; ecognidine as a topical anesthetic; edetic acid as an antioxidant; edoxudine as an antiviral; endothal as a defoliant; eosine as a yellowish cosmetic dye; esculin as a skin protectant; ethacridine as an antiseptic; euprocin dihydrochloride as a topical anesthetic; fenticonazole nitrate as a topical antifungal; fortimicin(s) as an antibacterial; fungichromin as a topical antifungal; gallic acid as an astringent, styptic; gentian violet as a topical anti-infective; gluconolactone as a cleaner; gossypol as a rubber antioxidant; heparin as an anticoagulant, hexamethylolmelamine as a fireproofing agent; mexamidine as an antiseptic, anti-acne; hydroquinine hydrochloride hemihydrate as a depigmentor; 1-(Hydroxymethyl)-5,5-dimethyl-hydantion as a cosmetic preservative; 8-Hydroxyquinoline sulfate as an antiperspirant, deodorant; iodic acid as an astringent; itraconazole as an antifungal; kanamycin(s) as an antibacterial; lactic acid as an acidulant; meralein sodium as a topical anti-infective; titanium powder or else as a muscle toner; ceramic powder or else as a temperature regulator; peppermint or menthol or derivatives thereof as a cooling agent; taurine as a stimulant; etc.

The active ingredients may be in the form of a formulation, a composition, a mixture, a preparation, a composite, a solution, a powder, a crystal or the like.

In a particular, but non-limiting implementation, the active ingredient is mixed with the other elements of the formulation, preferably prior to the formation of microparticles. Active ingredients having different properties may be added to the same formulation. Microparticles obtained from such a formulations will have a mix of the different active ingredients dispersed therein.

The active ingredient and the other elements of the formulation may be separable and uncompounded with each other. Alternatively, the active ingredient and the other elements of the formulation may be chemically bounded or may chemically interact. The types of possible interactions between the active ingredient and the other elements of the formulations depend, in part, on the nature of the active ingredient and the nature of the elements of the formulations.

The formulation may be homogenous or heterogeneous. A homogenous formulation includes a formulation of two or more substances that cannot be readily separated by common physical means (such as, for example, setting, filtration, etc). A heterogeneous formulation includes a formulation of two or more substances that can be readily separated by common physical means (such as, for example, setting, filtration, etc).

The active ingredient may be uniformly or a non-uniformly distributed within the microparticles. When the active ingredient is uniformly distributed in the microparticle, the concentration of active ingredient in the microparticle is steady as the microparticle disintegrates, whereas when the active ingredient is not uniformly distributed within the microparticle, the concentration of the active ingredient in the microparticle varies as the microparticle disintegrates. In other time release situations, the concentration of the active ingredient increases towards the center of the microparticle to compensate for reduced surface area as the microparticle disintegrates and thus tend to counteract the reduction of the rate of release of the active ingredient owing to the reduction of the surface area of the particle (as the particle shrinks due to erosion, its surface area diminishes).

The active ingredient may be hydrophobic or hydrophilic; preferably, the active ingredient is hydrophobic. In formulations where the active ingredient is not miscible with the carrier material, the active ingredient may, for example, be encapsulated in a material that is itself miscible with the carrier material so that the encapsulated active ingredient can be incorporated in the microparticles. For example, to incorporate a hydrophilic active ingredient in a microparticle composed primarily of a hydrophobic carrier material, it may be advantageous to encapsulate the hydrophilic active ingredient in a substance that is miscible with the hydrophobic carrier material of the microparticle. Examples of such substance include, but are not limited to, biocompatible polymers, such as polyethylene glycol; and amphipathic compounds such as soaps and detergents.

In a specific, but non-limiting implementation, the active ingredient is suitable for topical application and/or transdermal administration to a subject.

IV. Vehicles for Application of Formulations Comprising Microparticles

As intended by the present invention, application vehicles are useful for storage, transport and/or application of the microparticles. The application vehicle may for example, be a liquid body, a cream, a paste, a gel, a foam body or the like.

Preferably, the nature of the application vehicles is compatible with the composition of the microparticle as well as with the substrate onto which the microparticles are to be applied so as to avoid deterioration, degradation or weakening of the microparticles and/or substrate and/or any active ingredient that may be dispersed within the microparticles, and/or to avoid any other undesirable effects.

The amount of microparticles in the application vehicle may influence the state of the vehicle, i.e., whether the vehicle is a liquid, a paste, etc. The amount of microparticles also influences the viscosity of the vehicle, for example, the concentration of microparticles in a liquid vehicle is such that the viscosity of the liquid vehicle allows a substrate such as, for example, a textile, to be readily immersed into the liquid vehicle having the microparticles. The concentration of microparticles in a cream, gel or paste vehicle is such that the viscosity of the cream, gel or paste vehicle does not permit to readily immerse the substrate into the gel or paste vehicle but allows for the direct application of the vehicle onto the substrate such as, for example, by coating or spreading the application vehicle onto the substrate. Application of a cream, gel or paste vehicle to a substrate may be done using, for example, a knife, a blade, a Meyer Rod or may be done by rolling the application vehicle onto the substrate such as a foam sheet via, for example, a roller, or by direct application with the use of an analog roller, or serigraphy instrumentation or Flexo instrumentation or precision spray or deposit nozzles.

Ancillary agents may also be present in the application vehicle to facilitate the storage, transport and/or application of the application vehicle/microparticles as well as to facilitate or improve the activity or property of the active ingredient. Such ancillary agents may include: dies, antiseptic agents, anti-fungic agents, antibiotics, wetting agents, agents for hydrophobic treatment, surfactants, preservatives, color retention agents, emulsifiers, humectants, foaming/anti-foaming agents, anti-coagulating agents, stabilizers, antioxidants (to prevent oxidization), pharmaceutically acceptable carriers, diluents, excipients, among others.

In some implementations, the formulation from which the microparticles are obtained acts as the application vehicle. In these specific implementations, the formulation acting as application vehicle is the formulation not forming part of the microparticles.

In a specific, but non-limiting implementation, the application vehicle is applied to a support. As used herein, the term "support" includes applicators that may be used to transfer the formulation of microparticles to a substrate, wherein the substrate include an article of manufacture, the skin, etc. The support may be flexible, semi-flexible or non-flexible.

The surface of the support may be embossed, may have raised patterns, may have recesses or holes defined therein into which the formulation may be applied, such as, for example a polyethylene film embossed with a pattern such as a diamond pattern.

The support may be, for example, a polymer, more particularly a polyolefin, a foam, a non-woven material, a woven material, a paper release composition, a resin, a glass fiber, a carbon fiber, as well as known ductile metals such as aluminum, stainless steel, copper, silver or gold, or any combination thereof.

In a specific, but non-limiting, implementation, the application vehicle is applied to a polypropylene (also referred to herein as PPFV) support (FIG. 10A, element 1002) on which, for example, a square pattern of glass fiber has been applied (FIG. 10A, element 1000), thereby defining embossment and recesses on the surface of the polypropylene. The application vehicle may be prepared at a concentration of microparticles which is lower than the final concentration of microparticles desired. The application vehicle is applied to the PPFV so as to fill the recesses created by the pattern or glass fiber. The application vehicle/PPFV is then partially dried to evaporate part of the water from the application vehicle after which step, more application vehicle may be applied. This type of transfer is referred to herein as "humid transfer", where some water is transferred to the substrate. The resulting treated PPFV may be pressed against a substrate, such as for example a textile, to transfer the formulation of microparticles onto the substrate (FIG. 10B, element 1004).

It is also possible to let the treated PPFV dry completely so as to transfer very low water to the support. This type of transfer is referred to herein as "dry transfer", where very little or no water is transferred to the substrate. This type of transfer may be facilitated by the application of heat or ventilation. However, if heat is to be used, it should be carefully applied so as to prevent premature melting of the microparticles.

As used herein, the term "treated" refers to a material, a support, a substrate, an article, a textile, a fabric, etc. having the formulations and/or the microparticles as defined herein applied thereon. A treated material, support, substrate, article, textile, fabric, etc. has formulations and/or microparticles distributed therein.

As used herein, the term "distributed" includes microparticles that are retained in the pores or interstice of the material, support, substrate, article, textile, fabric, etc.; includes microparticles that are attached or fixed to the material, support, substrate, article, textile, fabric, etc.; and includes microparticles that have been absorbed by the material, support, substrate, article, textile, fabric, etc., and which upon being absorbed may or may not retain the microparticle shape.

V. Substrate

As used herein the term "substrate" includes materials onto which the formulation and/or microparticles are applied and from which the microparticle/active ingredient are released. Preferably, the substrate is porous. A porous substrate refers to a substrate that has interstices, recesses, pores or cross linkage openings in which the microparticles can be retained, impregnated or trapped. The interstices, recesses or cross linkage openings are preferably of a dimension that permits insertion and/or retention of the microparticles.

In some implementations of the present invention, the substrate is the skin of a human or an animal.

Specific examples of suitable substrates include, but are not limited to, fibrous textiles including natural fibers either vegetal (e.g., cotton, linen, jute) or animal (e.g., wool and silk) as well as mineral fibers (e.g., asbestos and viscose); chemical fibers either synthetic or artificial like polyester, nylon, acetate, polypropylene and rayon; paper and paper products; product made from composites; products made from wood or wood by-products, such as furniture materials and doors; products made from carbon fiber, products made from glass fiber, synthetic foam, such as polyethylene, polystyrene and polyurethane foam. Textiles may be woven, knitted or machine-knitted, or be present as a composite material (non-woven textile). In the case of composite materials, the fabric is not produced by wrap and weft or stitch formation, but by interlocking and/or cohesive and/or adhesive bonding of textile fibers. Non-woven fabrics are loose materials produced from spun fibers or filaments, in most cases made of polypropylene, polyester or viscose, the cohesion of which is generally provided by the fibers intrinsically holding together. In this regard, the individual fibers may have a preferred orientation (oriented or cross-laid non-woven fabrics), or be unoriented (entangled non-woven fabrics). The non-woven fabrics may be mechanically bonded by needle punching, stitching, or entangling by means of strong water jets. Adhesively bonded non-woven fabrics are produced by gluing the fibers together with liquid binding agents (for example, acrylate polymers, SBR/NBR, polyvinyl ester, polyurethane dispersions), or by melting or dissolving so-called binder fibers that are added to the non-woven fabric during its production. Non-woven material may be obtained from, for example, viscose, cotton, cellulose, jute, hemp, sisal, silk, wool, polypropylene, polyester, polyethylene terephthalate (PET), aramide, nylon, polyvinyl derivatives, polyurethanes, polylactide, polyhydroxyalkanoate, cellulose esters and/or polyethylene, and also mineral fibers, such as glass fibers or carbon fibers.

Examples of fabrics also include blends of dual or multiple fibers such as, but not limited to, polyester/elastane blends, polyamids, polyamide/elastane blends, cotton/polyester/elastane blends, polyacrylonitriles, acetates, modal, lyocell and linens.

Non-limiting examples of substrate onto or into which the formulation and/or microparticles may be applied include: clothing and accessories, bags and suitcases, personal cares, bandages, animal cares, toys, furniture, housing cleansing products, beddings, carpets/rugs, kitchen accessories, paints/decorations, agro textiles, geo-textiles, paper and pulp, plastic, ceramics, wood, glass, metal, leather, sporting articles, leisure and outdoor articles, tools, protective gears or the like.

The formulations and/or microparticles defined herein may be applied onto a finished article of manufacture, such as an article of clothing, bedding, etc. However, the formulations and/or microparticles may alternatively be applied to the material entering into the fabrication of the article of manufacture, prior to its production. For example, the formulations and/or microparticles defined herein may be coated onto a thread for sewing or weaving (e.g., a cotton, silk or nylon thread) entering into the fabrication of an article of manufacture (e.g., an article of clothing). Additionally, the treated thread may be further coated with a protective material to prevent premature release of the active ingredient. Such protective coating may comprise, for example, a wax component.

VI. Application of Microparticles to a Substrate

The type of interactions between the microparticles and the substrate can be of physical, chemical or electrical nature or may be of any combination thereof. Specific examples include, but are not limited to:
a) binding of the microparticles to the substrate by means of the binding agent which has chemical affinity for both;
b) entrapment of the microparticles within the substrate, facilitated by physical or non-covalent chemical manipulation of the substrate together with the microparticles in the presence of the binding agent; and
c) naturally-occurring chemical affinity which may occur between the surface of the microparticles and the substrate. These forces include hydrophobic interactions, hydrogen bonding, ionic or electrostatic interactions.

Figure 7:
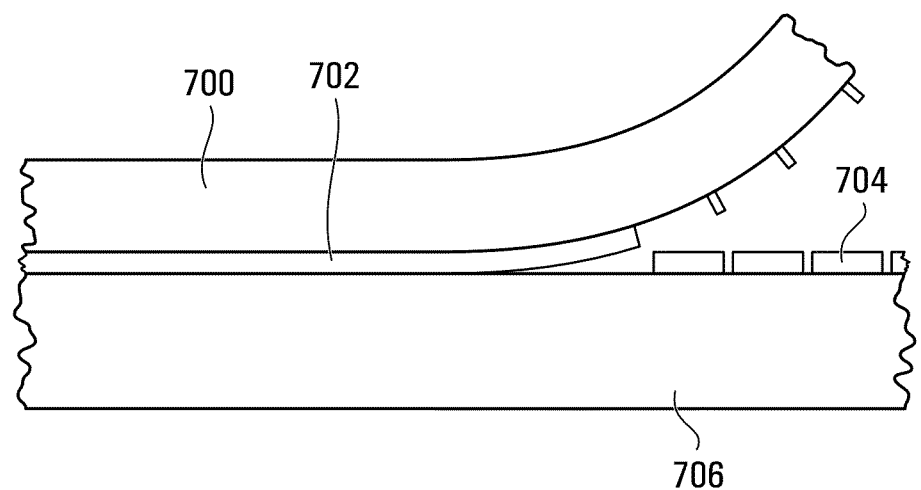
FIG. 7 is a schematic representation of a non-limiting example of a method for applying microparticles to a substrate using the technique of screen-printing.

In one specific aspect, the microparticles are applied to a substrate by transfer printing. The schematic representation at FIG. 7 illustrates how a formulation of microparticles may be transferred to a substrate using transfer printing. In this specific example, the formulation of microparticles (702) may be first applied to a solid support (700). This formulation may then be transferred (704) to a substrate (706) such as a textile when the support (700) is pressed against the substrate (706). This technique is well known in the art and is considered a versatile invention for applying designs to various solid objects.

In another specific, but non-limiting example, the microparticles may be applied to the substrate by screen-printing. The technique of screen-printing includes the technique of reproducing a stencil representing a design (such as a graphic design or logo) to an object using a flat screen or a cylinder screen made of a fine, porous fabric. These techniques are also referred to as serigraphy or stenciling method.

In this method, a stencil that represents the inverse (or negative) image of the design to be reproduced is created on a screen made of a fine, porous fabric that is stretched out over a frame. The stencil defines the areas where the design will not appear on the object to be printed and an application vehicle/formulation of microparticles as defined herein is placed on top of the screen, and the mesh openings are filled with the application vehicle/formulation of microparticles. An operator or an automatic system fills then applies the application vehicle/formulation of microparticles that is in the mesh openings to the object and the formulation of microparticles is transferred by capillary action to the substrate in a controlled and prescribed amount defined by the thickness of the stencil and the mesh. The frame is then removed from the surface of the object, leaving the formulation of microparticles upon its surface in the prescribed design. The technique of screen-printing is well known in the art and is known as a versatile technology that is used to print designs on a wide variety of objects including shirts, hats, polyethylene, polypropylene, paper, metals, wood, etc. and may be used to apply to a substrate the microparticles defined herein.

In a specific but non-limiting example, the microparticles comprising a prescribed pharmaceutical agent (or drug), are printed in a prescribed design on a substrate such as, for example, a shirt that can be worn by those in need of the pharmaceutical agent. By wearing this shirt, the wearer absorbs their prescribed dose of the active ingredient through the skin. In this specific example, the microparticles may be suspended in a liquid or semi-liquid application vehicle that may also be used solely or combined with dye or ink to help identify when the dose is exhausted. Each shirt is turned inside out and then put on a support that is used to hold the shirt while the liquid application vehicle is being applied. Non-permeable material is then applied to a fine mesh of porous fabric (such as for example, PPFV) stretched over a frame to form the inverse (negative) image of the design to be printed on the shirt. The application vehicle is then applied to the mesh and a bar is used to distribute the application vehicle along the mesh, filling the spaces within the mesh with the application vehicle containing the microparticles. The frame is then applied to the surface of the shirt and then a spongious material, such as a squeegee (or rubber blade) is passed over the mesh to force the liquid application vehicle onto the surface of the shirt. The application vehicle that is contained in the mesh openings is transferred to the shirt. The process may be repeated with other stencils and application vehicles to apply other designs and other active ingredients to the shirt. Once all designs and all application vehicles have been applied, the shirt is then removed from the support, dried and then turned inside-out again so that the surface of the shirt onto which the liquid material was applied is now on the inside of the shirt and will be physically in contact with the skin of the wearer.

The technique of ink-jet printing includes propelling variably sized droplets of liquid or melted material (such as dye or ink) onto an object, fabric or substrate. Unlike the transfer and the screen printing techniques discussed above, ink-jet printing applies the compound or ink to be printed directly to the material itself, without having to transfer the material to an intermediary, such as a frame. This technique may require a computer to control the ink-jet printing equipment that is used to deliver the ink (or other material) onto the substrate according to a certain pattern. This technique is well known in the art and is known as a very versatile technology that can be cheaply and reliably used to print designs on a wide variety of materials, including most paper products, as well as thin fabrics (e.g., cotton) made of natural or artificial fibers. This technique may also be used to apply the microparticles as defined herein to an object.

Figure 8:
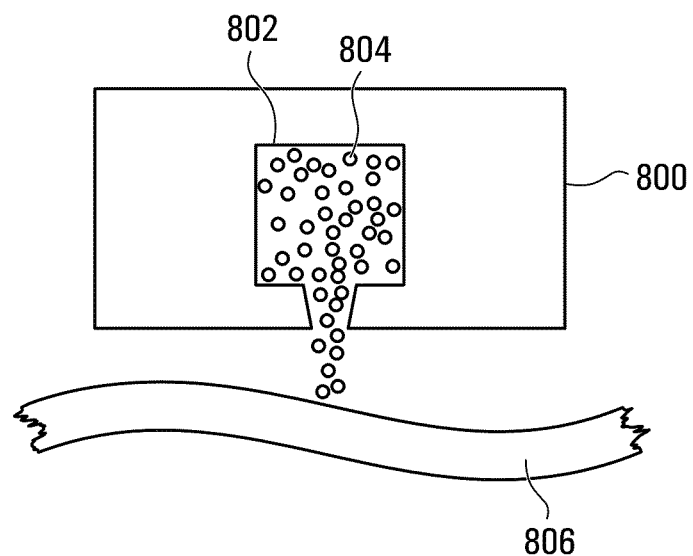
FIG. 8 is a schematic representation of a non-limiting example of a method for applying microparticles to a substrate using the technique of ink-jet printing.

The schematic representation of FIG. 8 illustrates an example of how a formulation of microparticles/active ingredients may be transferred to a textile using an ink-jet printer. In this example, the cartridge (802) of the ink-jet printer (800) is filled with the application vehicle/formulation of microparticles (804) and is inserted into an ink-jet printer that is connected to a computer and controlled by a software application running on the computer. The ink-jet printer applies the application vehicle/formulation of microparticles (804) directly to the surface of the substrate (806) in the prescribed design under the direction of a software application running on a computer.

In a further aspect, the formulation of microparticles may be applied to a substrate by use of pressing rollers. This technique may be used where it is necessary to apply the formulation of microparticles consistently across and throughout the substrate, as well as in cases where an earlier usage of the printing technique either did not transfer sufficient amounts of the formulation or did not saturate the substrate sufficiently.

Another variant on the use of this technique may be seen from the previous non-limiting example used to illustrate the transfer printing technique. In this example, a porous material containing the application vehicle is applied against a substrate to transfer the microparticles in a desired design. Additionally, pressing rollers may be used to compress the porous material onto the substrate under pressure, thus enabling the transfer of the microparticles onto the substrate.

Pressing rollers could also be used to transfer a predetermined design in a gel form. Pressure is used to release the predetermined design onto an article of manufacture.

The dose or amount of active ingredient to be applied to a substrate, the distribution of the active ingredient on the substrate, and the period of exposure to the active ingredient depend on the effect or manifestation desired and on the nature of the active ingredient. The dose, distribution and period of exposure of active ingredient will thus be apparent to a person skilled in the relevant art.

VII. Release of the Active Ingredient

Microparticles are released from the substrate when the microparticles are subjected to progressive erosion and/or degradation caused by one or more stimuli or when the treated substrate is subjected to stimuli that cause progressive erosion and/or degradation of the microparticles or simply when the microparticles are detached from the substrate.

The overall physical structure of the microparticles is affected by stimulus which weakens or breaks the interactions between the microparticles and the substrate so as to release or detach the microparticles from the substrate. A stimulus does not affect each microparticle in a population of microparticles evenly giving rise to a progressive erosion, destruction and/or release of the microparticles.

As used herein, the term "progressive erosion" or "progressive destruction" or "progressive release" refers to the progressive disintegration of the microparticles causing gradual release of an active ingredient dispersed therein. As the microparticles disintegrate, the active ingredient is released from the microparticles.

In a specific implementation, the release of microparticles and active ingredient from the substrate is relatively continuous and constant.

Erosion may cause all or part of the microparticles to be released from a substrate or may cause detachment of all or part of the microparticles from the substrate. Released or detached microparticles may fall from the substrate or may remain in the substrate to form, for example, a homogeneous film.

Stimuli that cause progressive erosion, destruction or detachment of the microparticles include, but are not limited to, physical stimuli, chemical stimuli or electrical stimuli. A physical stimulus may be such as a mechanical contact with the treated substrate, rubbing or vibration of the substrate, heat that may or may not be involved in mechanical contact. A chemical stimulus may be such as the exposure to a chemical agent, a change in pH, a change in salt concentration, exposure to microbes or toxin secreted by microbes, a change in temperature and a change in humidity or the like.

In another specific, but non-limiting implementation of the present invention, the intensity of the stimulus determines the degree of release of the active ingredient and the period over which the active ingredient is released. For example, the normal body heat of a person may be sufficient to cause the destruction of the microparticles and release of the active ingredient. In a non-limiting example, the chemical stimulus may be a component of human sweat that causes the progressive erosion of the microparticles and the release of the active ingredient. Body heat produced by physical exertion through exercise (which may also be accompanied by increased sweat production) may increase the degree at which the active ingredient is released.

Without intent to be limiting, many factors may be involved in releasing microparticles and active ingredient from a substrate. In a situation where, for example, a treated substrate is placed in contact with the skin, the temperature and the pH of the skin may cause or influence the release or disintegration of the microparticles. The temperature of the skin may cause the microparticles to melt. Acidity or alkalinity of the skin may affect the components of the microparticles so as to cause their disintegration. Normal skin surface pH is between 4 and 6.5 in healthy people, though it varies among the different areas of the skin. Skin surface pH below 4 or above 6.5 may affect the integrity of the microparticles. The skin also secretes chemical substances that may affect the integrity of the microparticles.

The microparticles may be in contact with the areas of the skin which is subjected to frequent movement such at articulations and/or joints (e.g., at elbows, ankles, knees or the neck). Skin movement at these areas may be more frequent than at other areas of the body where there are no articulations and/or joints. Movement of the skin creates friction which may be accompanied by an increase in local temperature of the skin thus affecting the integrity of the microparticles.

In a further implementation, the active ingredient is released from the substrate in response to a predetermined stimulus. In this specific implementation, the stimulus is functionally related with the active ingredient to be released. For example, a coagulant may be released from a substrate when the substrate is placed in contact with blood or a cooling agent may be released from a substrate upon exposure to heat.

Progressive erosion can also result from mechanical action producing wearing of the surface of the microparticles, such as when the microparticles are in contact with an external body or are rubbed against the substrate itself; can result from melting of the surface of the microparticles as a result of application of heat or as the result of application of a chemical agent; can result from application of chemical agent that degrades the substrate and/or degrades the microparticles.

In some aspects, the release of the active ingredient is gradual, in some other aspects; the release of the active ingredient is steady during the entire life of the microparticle. Alternatively, the release of the active ingredient may be variable throughout the life of the microparticle. Release of the active ingredient is measured per unit area of surface of treated substrate over time.

In one aspect, progressive erosion of the microparticle and the gradual release of the active ingredient relate to, for example, the intensity of the stimulus applied to the microparticle and/or the substrate, the distribution profile of the microparticles in the substrate, the nature of the formulation and the nature of the active ingredients. The factors influencing the gradual release of an active ingredient from the substrate will be readily appreciated by those of skill in the art.

In one specific but non-limiting implementation, articles of manufacture having microparticles distributed therein still release microparticles, and the active ingredient dispersed therein, after 5, 10, 15, 20, 25, 30, 35, 40, 45, 50, 55 or 60 wash cycles.

In a further implementation, articles of manufacture having been through 5, 10, 15, 20, 25, 30, 35, 40, 45, 50, 55 and 60 wash cycles still maintains a positive active ingredient release rate. The expression "positive active ingredient release rate" indicates that microparticles and therefore the active ingredient dispersed therein are still being released from the substrate.

In a further aspect, articles of manufacture having the microparticles distributed therein still retain microparticles and the active ingredient dispersed therein after 60, 55, 50, 45, 40, 35, 30, 25, 20, 15, 10 or 5 wash cycles.

Figure 9A:
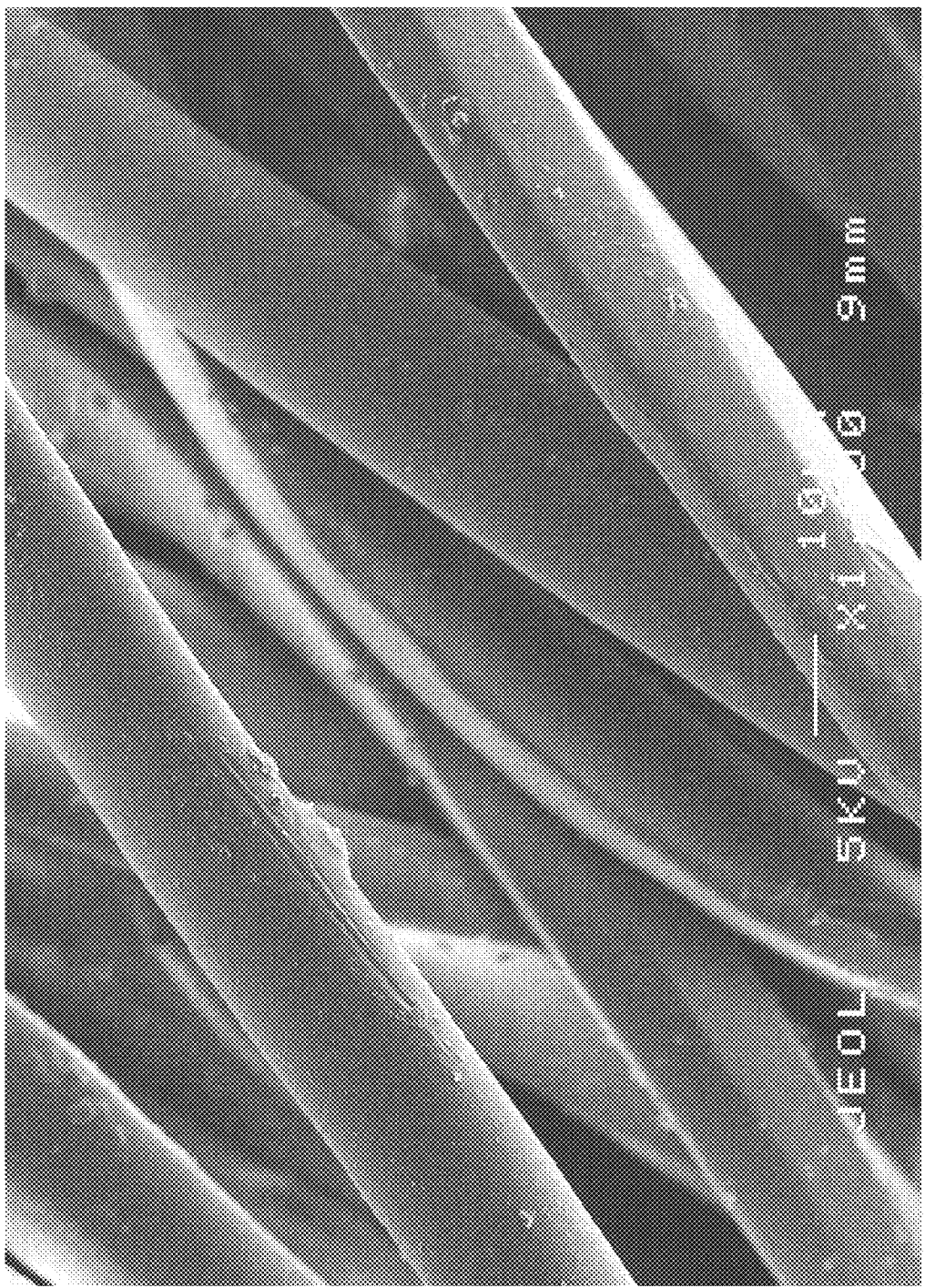
FIGS. 9A and 9B are electron micrograph pictures of a polyester substrate impregnated with microparticles obtained from a TPMAGMS formulation after 30 wash cycles (FIG. 9B) and a virgin polyester substrate (no microparticles applied) after five wash cycles (FIG. 9A).
Figure 9B:
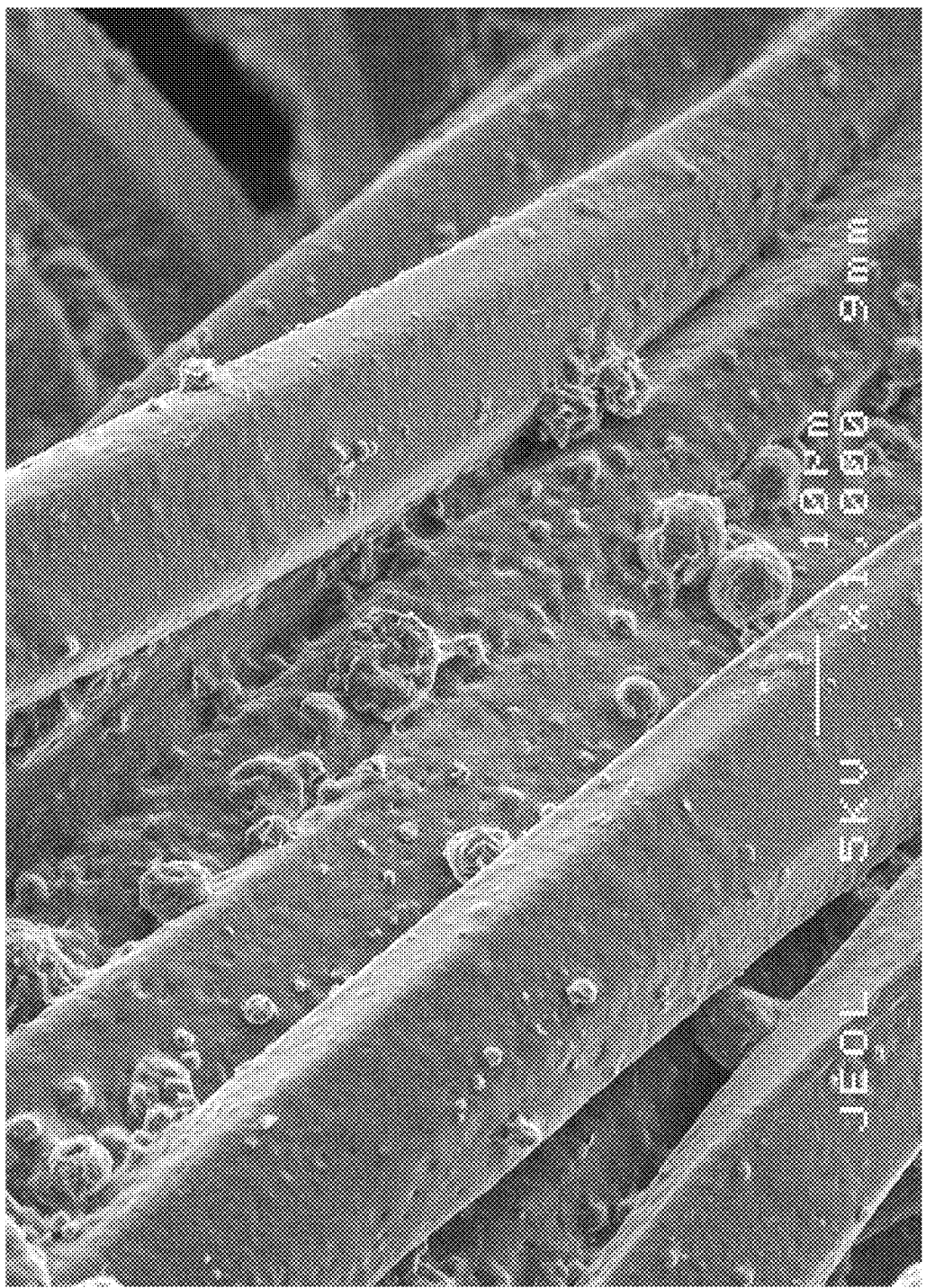

In a specific, but non-limiting example, the electron micrograph shown in FIG. 9B, demonstrates the microparticles obtained from a TPMAGMS formulation attached to a polyester textile after 30 wash cycles (FIG. 9B). The microparticles can be distinguished when comparing FIG. 9B with a non-treated polyester textile (virgin) subjected to five wash cycles (FIG. 9A).

In a further specific implementation of the present invention, the formulations defined herein comprising an active ingredient are directly applied to a substrate without first obtaining microparticles, by for example, using formulations that do not have binding agent. Such implementation is advantageous in situations where, for example, a fast release of the active ingredient from the substrate is desirable.

VIII. Release Index

In one aspect, the present invention provides for a method of improving stabilization of one or more active ingredient in an article of manufacture such as a fabric, textile, fibers, foam or the like. The formulations of microparticles as defined herein, present several advantages for use in this method. For example, the physical and chemical properties of the microparticles allow them to reach the interstices, pores or cross linkage openings of a porous substrate and to be retained, trapped, attached or fixed into these interstices, pores, cavities or cross linkage openings. Because the microparticles reach the inner core of the substrate, it gives rise to a progressive erosion and/or disintegration of the microparticles and its gradual release from the substrate, thereby giving rise to gradual release of the active ingredient. Other factors influencing the progressive release of microparticles from the substrate include the nature of the substrate, the presence and the concentration of a binding agent as well as the nature of the surfactant.

In a specific, but non-limiting implementation, the addition of a cationic surfactant in the formulation creates an overall residual positive charge on the surface of the microparticles. The positively charged microparticles adhere to, by charge neutralization, or are absorbed by, the fibers of a textile which are generally negatively charged. Adherence of the microparticles to the textile is also increased by the addition of a binding agent into the formulation, which binding agent itself adheres to the fibers of the textile bridging them to the microparticles.

The advantages of treating an article of manufacture with the formulations of microparticles defined herein can be appreciated by, for example, the resistance of the microparticles to wash cycles. As shown in FIG. 1, the percent of microparticles released from a substrate of polyester (referred to as P100t) and a treated substrate of nylon-cotton (in proportion of 70-30; referred to as N70C30) treated with a TPGMS formulation of microparticles or a TPMAGMS formulation of microparticles. The substrate made of nylon-cotton has slightly better retention properties than the substrate made of P100t. The data presented in FIG. 1 also indicates that microparticles made from a TPMAGMS formulation have good adherence properties to cotton fibers.

Figure 2:
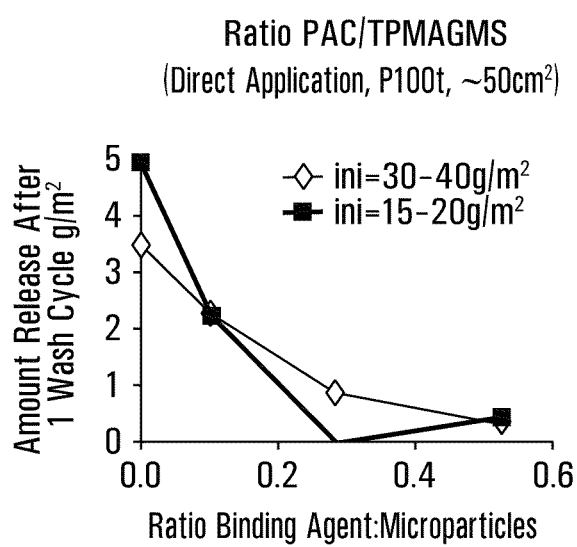
FIG. 2 is a graph showing the influence of the ratio of binding agent:microparticles on the retention of microparticles in the substrate after one wash cycle. The term "ini" refers to the initial amount of formulation applied to the substrate.

The influence of a binding agent on the release of microparticles is also exemplified in FIG. 2 which shows that increasing the ration of PAC/TPMAGMS in a formulation, increases the resistance of the microparticles to wash cycles.

An appreciation of the rate of release of microparticles from a substrate may be obtained by, for example, calculating the release index. As used herein, the "release index" refers to a constant associated with the rate of release of microparticles from a given surface of treated substrate over time. More particularly, the release index is a representation of the decrease in mass of microparticles per a given surface of treated substrate over time. In one aspect of the present invention, the release index is in the range of about 1 to about 20, preferably in the range of about 2 to about 7, and more preferably in the range of about 4 to about 6.

IX. Perception Indicators

In a further non-limiting aspect, the present invention allows to create articles of manufacture having perception indicators that are functionally related to the presence, the nature and/or the amount of active ingredient.

The perception indicators provide information regarding the presence and distribution of the microparticles and active ingredients on the substrate, provide information on the type of active ingredient available at certain locations on the treated substrate and provide information regarding the amount of active ingredients remaining on, or released from the treated substrate.

A perception indicator may be a visual indicator, an olfactory indicator, a tactile (or feel) or a sonic indicator.

A visual indicator may be such as a distinguishable pattern, a color indicator, single- or multi-colored patterns, single- or multi-colored icons and pictograms, such as an emoticon; single- or multi-colored alphanumeric text, symbols, such and logos or the like.

In a specific aspect, the visual indicator indicates the location of active zones; wherein an active zone refers to a zone on the article having been applied with the active ingredient (or with the microparticles comprising it).

In a further specific, but non-limiting implementation, the presence of different active ingredients within the same substrate may be correlated with different perception indicators (such as a different color, motif or pattern) to inform of the location of these active ingredients and how the substrate should be disposed of to achieve the best results.

The perception indicator also acts as wear indicator. A wear indicator shows how much active ingredient has been released from the substrate and/or how much active ingredient remains, and indicates when the treated substrate needs to be replenished with the active ingredient. For example, a dye may be added to the formulation of microparticles and transferred to the substrate to indicate the location of the microparticles. As the microparticles are released from the substrate the intensity of the dye diminishes providing the user with an appreciation of how much microparticles/active ingredient remains (or has been released) from the substrate.

Examples of olfactory perception indicators include, but are not limited to, a fragrance or a perfume that is applied to the substrate and which indicates the presence of an active ingredient. Preferably, the odor indicator is proportional to the amount of active ingredient present on the substrate and as the active ingredient diminishes, the odor indicator diminishes accordingly.

The perception indicator may also be a tactile or feel indicator which is perceived by the skin of the user as a physical sensation. In some implementations, application of the microparticles to the substrate creates a relief or embossments on the substrate that are felt by the skin of the user. Such relief or embossments indicate the location on the substrate of the active ingredient. Preferably, as the active ingredient diminishes, the relief or embossments diminishes accordingly. In some particular implementations, the tactile or feel indicator may also micro-massage the area of the skin it is in contact with or may exfoliate it.

In some further implementations of the present invention, the perception indicator indicates how much active ingredient is present at different locations on the substrate. Preferably, the perception indicator is adjusted so as to be proportional to the release of the active ingredient, i.e., the perception indicator diminishes proportionally to the diminution of the active ingredient.

X. Methods for Manufacturing Perception Indicators

Perception indicators may be obtained, for example, by transferring, printing, spraying, spreading, applying, impregnating or saturating a formulation of microparticles onto a substrate so as to form a perception indicator. The indicator may be used in a number of formats, shapes, colors and textures.

In a specific, but non-limiting implementation, the perception indicator may be applied onto the substrate to cover any where between about 0.01% to about 99% of the total surface of the substrate. Preferably, the perception indicator should be applied onto a substrate so as to maintain the desired initial properties of the substrate such as for example, its flexibility, its breathability, or the like.

Figure 13:
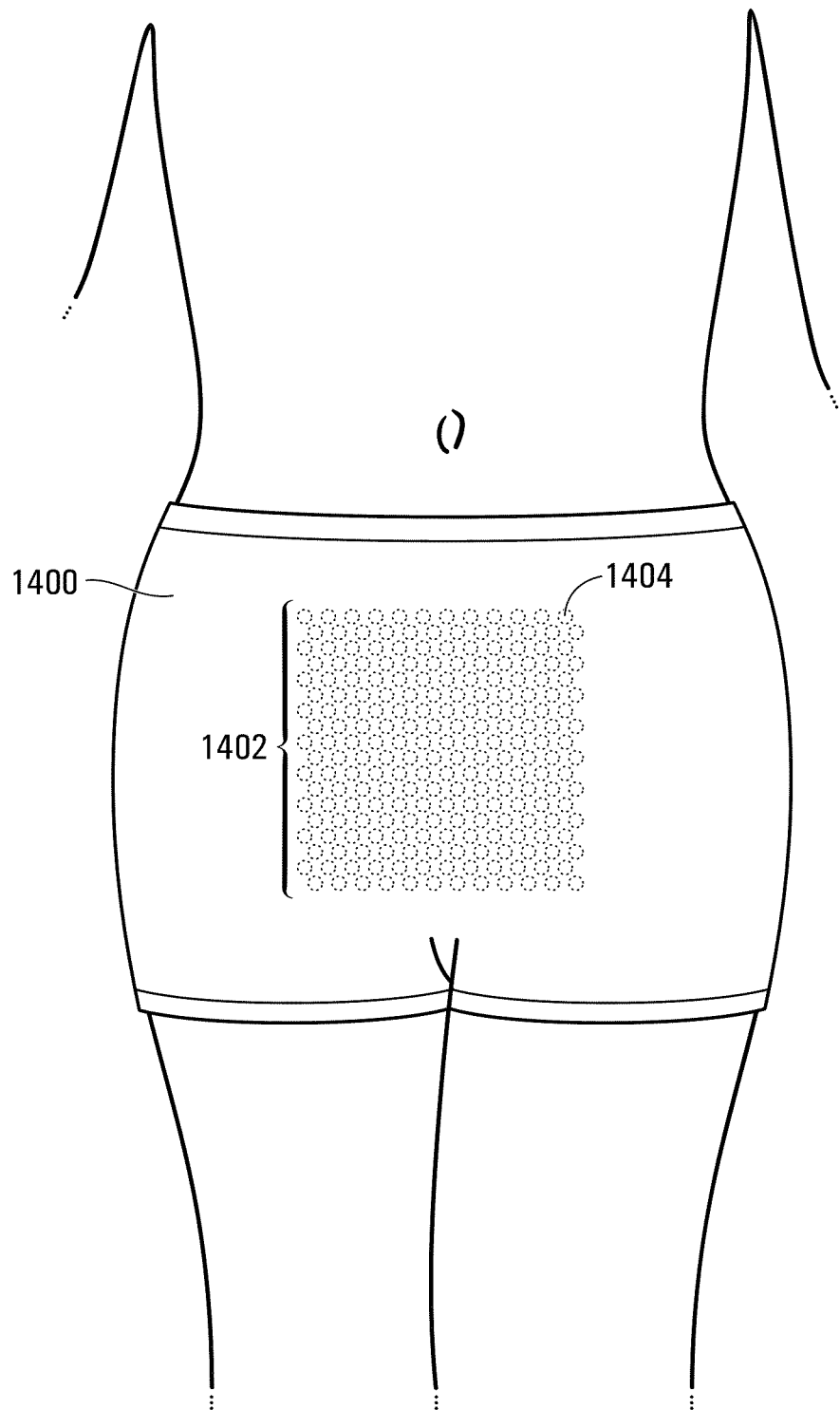

The perception indicator may also be applied onto the substrate in a repetitive pattern. The pattern may occupy any where between about 0.01 mm to about 20 cm per $m^2$ of the substrate and may repeat itself over a given surface area of the substrate. For example, the repetitive pattern has the shape of a circle having a given diameter that is repeated aver a given surface of a substrate such as for example, a textile. FIG. 13 is a schematic representation of an undergarment for women (1400) onto the inner surface of which has been applied a formulation of microparticles in repetitive circles. As seen on FIG. 13, the circles (1404) are disposed on a repetitive pattern (1402) over a given surface of the substrate. A sufficient amount of formulation is applied to form each circle (1404) and to create a relief on the substrate that can be felt by the skin. In this example, the microparticles that are applied to this undergarment may comprise such active ingredients as slimming agents. Preferably, the repetitive pattern is applied onto the substrate so as to allow the substrate to retain its properties such as flexibility and breathability.

In the following non-limiting example for the manufacture and use of a visual indicator, the material to which the microparticles are to be applied may for example be insoles to be inserted within shoes. To prevent and/or retard the growth of bacteria and fungi within the insole and keep the shoe smelling fresh, a formulation of microparticles having a deodorizing agent as an active ingredient is applied to the insole of a shoe through for example, the PPFV technology defined herein. An anti-bacterial agent, an anti-fungal agent and a dye-based visual indicator may also be included in the formulation and in the microparticles. These agents may also be included in the application vehicle.

The formulation of microparticles comprising a dye-based indicator may be applied, for example, in the pattern of a corporate logo within the area of the insole that is normally resides under the heel of the foot. The dye-based indicator is tied to the general level of the active deodorant agent within the insole, so that as the active ingredient is discharged, the logo created from the dye appears to fade until the active ingredient is exhausted and the logo completely disappears. Once the logo disappears, the user knows he must either replenish the active ingredient with the insole or replace the insole to avoid unpleasant foot odor.

In the following non-limiting example for the manufacture and use of an olfactory indicator, an article of manufacture upon which the formulation of microparticles is to be applied is a shirt. In this specific example, the perception indicator is the fragrance itself, which is incorporated within microparticles that are activated by body heat to erode and release the fragrance into the surrounding air. The formulation of microparticles containing the fragrance is applied to the shirt. As the amount of microparticles and active ingredient decreases over time, the smell of the fragrance becomes successively less and less noticeable until it disappears completely when the active ingredient is exhausted.

While in this non-limiting example, both the active ingredient and olfactory indicator were identical, it is conceivable that the olfactory indicator may be different than the active ingredient. In such a case, the olfactory indicator would be tied to the level of the active ingredient such that the level of the active ingredient could be determined by the intensity of the scent or fragrance. For example, the active ingredient incorporated within the shirt may be a therapeutical agent such as a drug. In this case, the olfactory indicator would be tied to the amount of the drug within the shirt such that a wearer would be able to determine the amount of drug remaining on the substrate.

In the following non-limiting example for the manufacture and use of a tactile indicator, the active ingredient may be, for example, a medicinal agent or drug suitable for children. The present invention is used in the capacity of placing a predefined dosage of the active ingredient for a period of several days onto for example, the underside of a wristband (i.e., the side that is in contact with the skin), which the child wears on their wrist or arm. By placing the medicinal agent in contact with the skin, the child receives their prescribed dosage of the drug without having to actively remember to take it each day. In this specific example, the microparticles containing the drug may also comprise a foaming agent that solidifies in the presence of a particular frequency of ultraviolet (UV) light. The formulation of microparticles may be applied to the underside of the wristband via a gel application vehicle using a solid support (such as for example, a PPFV) that applies the formulation to the substrate in identifiable and predictable patterns (e.g., stripes, crosses, waves or the like). Once applied, the UV light is applied to the wristband that causes the foaming agent to solidify into a raised pattern. Upon initial application, the raised pattern created by the foaming agent can be identified easily. However, as the microparticles containing the active ingredient are eroded and more and more of the drug as well as the foaming agent are dispensed the pattern on the underside of the wristband wears down.

There are various other possible perception indicators and various other possible applications using the invention defined herein which are all encompassed by the present specification.

XI. Methods for Replenishing a Treated Article of Manufacture

In a further implementation of the present invention, it is desirable to replenish or reactivate a treated article of manufacture with further active ingredient in situations where, for example, the active ingredient on the treated article has diminished or vanished in response to a stimulus, or after the treated article has been through various wash cycles, or in situations where an increase in the concentration of active ingredient on the treated article is required, or to add a further active ingredient to a treated article.

Replenishing or reactivating a treated article extends the life of the active ingredient in the treated article, thereby prolonging the release of the active ingredient from the article and the duration of the beneficial properties procured by the active ingredient.

Methods for reactivation or for replenishing a substrate (or article of manufacture) include methods of applying a formulation of microparticles to a substrate as defined herein. Other methods are also useful such as, but not limited to, the use of treated patches or pads which can be applied to individual article of manufacture. In this specific, but non-limiting example, a formulation of microparticles may be transferred from a treated patch or a treated pad to a selected area of the article by contacting the treated surface of the patch or pad with the surface of the substrate in need of further active ingredient. The transfer may be performed by applying pressure to the patch or the pad. The pressure may be provided by using, for example, pressing rollers or by ironing the patch at a temperature that will preclude premature melting of the microparticles. A solution comprising the formulation of microparticles may also be sprayed onto selected areas of the article of manufacture or may be spread.

In some implementations, the patches or pads are applied directly onto the skin of the user. The patches may be transdermal adhesive patches to deliver a specific dose of medication through the skin and into the bloodstream; nicotine patches that releases nicotine into the body; contraceptive patches that releases contraceptive (such as synthetic estrogen and progestin hormones) to the body; dermatological patches that release a dermatological ingredient to the skin. Such patches may be made in different shapes and design and may be harboring different colors. For example, a pad having the shape of an eye mask and being treated with microparticles comprising as active ingredient colostrums, such as for example bovine colostrums, may be applied onto the eyes of the wearer and the colostrums is delivered to the skin around the eyes of the wearer.

In a further specific, but non-limiting implementation, refill containers filled with formulations of microparticles defined herein are used to re-apply the active ingredient to the article. The refill containers may be in the from of, for example, a can, a bag, a pouch, or the like and their content may be spread, sprayed, poured, applied, transferred, impregnated or printed onto the article. The article may also be soaked and/or rinsed in the formulation of microparticles or in a milieu comprising a formulation of microparticles. For example, an article to be replenished or reactivated with an active ingredient may be placed in a domestic washing machine into which the content of the refill container has been placed or into which sheets of fabric softener onto which the formulations defined herein have been applied have been placed.

In this specific example, the microparticles enter in contact with the article and are trapped on the article. Such method is useful in situations where, for example, release of the active ingredient is to be achieved over a very short period of time as the application of the formulations of microparticles may resist few wash cycles.

In a further example, treated articles are manufactured from a treated substrate such as a treated fabric, fibers or textile. The treated substrate may be transported in rolls or bales to the location where the articles are to be manufactured. During transportation, it is possible for microparticles to be released by mechanical stimuli and it may be advantageous to add such microparticles to the substrate prior to incorporation of the substrate into the article. Therefore, the invention defined here allows the end user of the present invention to incorporate formulation of microparticles having the desired active ingredient at the time the substrate is converted into an article.

For example, the article to be replenished with an active ingredient may be a shirt that contains microparticles embedded in the region of the underarms. The formulation of microparticles applied via a solid support (such as, for example, PPFV) contains a deodorant, a fragrance and a color indicator that are released with normal body heat to provide deodorizing properties to the wearer. The color indicator also disappears over time as the microparticles are eroded and the active ingredients within the shirt are exhausted. The shirt may be sold with press-on patches that are used to replenish the active ingredients, once the visual indicator shows that these agents are exhausted. Since a single patch is used to replenish the active ingredient in one region of the shirt, patches may typically be sold in even-numbered quantities, such as 2, 4 or 8 patches. It should be appreciated that patches may also be purchased independently of the shirt and may apply different fragrances upon application. Each patch used to replenish the active ingredients in a shirt may have a color top side that differs with the fragrance applied, as well as a different color underside that contains the microparticles having the deodorant and fragrance. The difference in the appearance of the sides of the patch ensures that a wearer does not apply the wrong side of the patch during the replenishment procedure outlined below. The underside of the patch may also be embossed so as to leave a visual pattern on the shirt.

To replenish the active ingredient, the shirt is turned inside out and the patch is aligned with the area in the underarm region, with the top (colored) side facing up. Pressure is applied to the top (colored) side of the patch for a duration sufficient to transfer the microparticles from the substrate on the underside of the patch to the material in the shirt. This procedure also causes the visual indicator, corresponding to the embossed surface of the patch, to reappear on the shirt, indicating that the active ingredients have been replenished.

XII. Examples of Practical Applications

The following examples demonstrate specific utilities and usefulness of the invention in several non-limiting scenarios and are intended to provide the reader with an indication of how the invention defined herein may be applied in several industries, including the following:

Cosmetotextile: The invention defined herein is also useful in the field of cosmetotextile. The field of cosmetotextile relates to articles of manufacture made of textile and which comprise a substance or a formulation to be released from the textile onto one or more parts of the human body, wherein the substance or formulation serves an esthetical purpose. In the cosmetotextile field, the invention defined herein may be used to produce for example, upper-body-clothing articles that contain samples of for example, but not limited to, perfume or cologne, anti-aging creams, new depilatory lotion, anti-cellulite treatment, slimming treatment.

Clothing: Manufacturers of clothing articles (shirts, pants, socks, or the like) or fashion accessories (belts, hats, or the like) may use the invention to deliver agents for cosmetic or therapeutic purposes, such as athletic socks that contain a deodorant that is released during and after exercise, pants that contain an anti-cellulite treatment or night masks with anti-wrinkle agents.

Therapeutic: pharmaceutical companies, biotechnology companies and other may use the present invention to deliver topically or transdermally one or more therapeutic agents to a subject.

Luggage: Producers of luggage (such as suitcases, briefcases, etc.) may use the invention to deliver agents for cosmetic purposes, such as suitcase interiors.

Personal Care products: Producers of personal care products (such as creams or soaps) may use the invention to deliver agents for cosmetic or therapeutic purposes, such as a bath towel that contains moisturizing and firming agents, furniture cleaning spray that also contains UV-blocking products and to maintain and extend the vibrancy of colors used for fabrics that are continually exposed to the sun, such as lawn furniture pillows and cushions, textiles or fabrics that contain insect repellents.

Toys: Manufacturers of toys designed for use by humans may use the invention to deliver agents for pharmaceutical or hygienic purposes, such as a baby pacifier that delivers pre-determined doses of medicine. The invention may also be applied to toys designed for animals.

Furniture and Housing Products: Producers of furniture may use the invention to deliver agents for cosmetic or for conservation purposes such as sprays, creams and foaming gels that maintain the cleanliness and deodorization of the fabrics.

Carpets and Rugs: Manufacturers of carpets and rugs may use the invention to deliver agents for cosmetic purposes, such as sprays or creams that apply pedicure treatment to the users. The invention defined herein may also be used to deliver anti-histaminic agents.

Kitchen accessories: Producers of kitchen accessories may use the invention to deliver agents for cosmetic or hygienic and cleansing purposes, such as paper towels that release fragrance, soap and/or detergents while absorbing waste liquids.

Agro-textiles: Manufacturers of textiles for agricultural uses (referred to as agro-textiles) may use the invention for prevention or industrial purposes, such as for bags of animal feed that would contain pesticides on the exterior of the bag to kill pests while containing a hygroscopic substance on the interior of the bag that would absorb humidity and keep the feed materials dry.

Geo-textiles: Producers of textiles for use in building and construction (referred to as geo textiles) may use the invention for added value purposes such as, for example, producing screens with fog preventing agents.

Sports, Leisure and Outdoor products: Producers of sport, leisure and outdoor products may use the invention for cosmetic or therapeutic purposes, such as to produce camping equipment with built-in insect repellent.

Transportation: Manufacturers of vehicles may use the invention for cosmetic purposes, such as to integrate deodorant or therapeutic fragrances into the fabric used in seats for mass transit vehicles, like trains, planes and automobiles.

In a more specific, but non-limiting example of practical application, the present invention relates to the manufacture of a treated glove, the inner side of which (i.e., the side of the glove in contact with the skin of the hand of the wearer) is treated with the microparticles defined herein. In this implementation, the treated glove is made of a cotton blend. The active ingredient is a dermatological agent that reduces skin irritation such as a corticosteroid and a moisturizer to improve the skin's overall hydration. The microparticles having the active ingredients dispersed therein are prepared using a formulation such as defined herein. Namely, the elements of the formulation including the dermatological agent and the moisturizer are mixed together. The mixed formulation is emulsified to created microparticles. A solid support is used to transfer the formulation comprising the microparticles onto the interior surface of the gloves. The solid support consists of a mould of a hand that would fit inside the glove and that is created from a PPFV fiber with dispersion mechanism located at the end of each finger where the fingertip would normally be located. This mechanism disperses a predefined amount of the formulation at the end of each glove finger. The glove is then removed from the mould and inserted between two moving rollers spaced appropriately to compress the glove and to spread the formulation on the inner surface of he glove. By inserting the finger-end of the glove between the rollers first, the rollers both remove forces the formulation that was deposited by the mechanism at the fingertip upwards towards the open end of the glove. This step ensures that the formulation is distributed throughout the glove's interior surface while also increasing the amount of microparticles that are impregnated into the cotton fibers of the glove.

In a variant of this implementation, the blended cotton spandex textile is first treated with the formulation comprising the microparticles. The formulation is applied onto the textile by using pressing rollers. The treated textile is cut and sewed in a glove shape with the treated surface of the textile corresponding to the inner surface of the glove (i.e., the surface in contact with the skin of the wearer).

Such treated gloves can be used as inner gloves. For example, the treated gloves may be placed in work gloves and safety gloves (e.g., barbed wire handler's gloves, chainsaw gloves, fireman's gauntlets, welder's gloves, aircrew gloves: fire resistant, sandblasting gloves, gardening gloves, impact gloves, rubber gloves, sport and recreational gloves). Such treated gloves can also be placed in medical gloves such as those used by health care professionals (e.g., latex gloves or surgical gloves). As used herein, the term "gloves" includes mittens and other variants of garments that cover the hand of a wearer.

A person skilled in the art will appreciate that variations of this implementation may be introduced without departing from the resulting treated gloves.

In a more specific, but non-limiting example of practical application, the present invention relates to the manufacture of a treated bandage for use in the preparation of orthopedic casts, such as plaster bandages. Typically, plaster bandages consist of a cotton bandage that has been impregnated with plaster of paris, which hardens after it has been made wet. In this application, the first layer of cotton bandage which comes in contact with the skin of the patient, is treated with a formulation of microparticles comprising a therapeutic agent such as an antibiotic to prevent and/or treat any lesions on the skin that is to be covered by the cast as well as a moisturizer or a calming lotion.

As defined above, the formulation is prepared my mixing the elements including the active ingredients and microparticles are obtained by emulsifying the mixed formulation. The cotton bandage is impregnated with the microparticles by either soaking the bandage into the formulation comprising microparticles or by applying the formulation onto the bandages using for example, pressing rollers. The treated bandages are dried and then applied directly onto the skin of the patient. Subsequent layers of the bandages that have been impregnated with plaster of paris are applied onto the treated bandage to create the cast. As will be readily appreciated by a person skilled in the relevant art, the present invention may also be used in the preparation of many other types of prosthesis.

In another specific example of practical application, the present invention relates to the manufacture of bed sheets that are impregnated with a formulation comprising microparticles having an active therapeutical agent dispersed therein. In this application, the application vehicle may be a liquid, a gel or an aerosol spray comprising the microparticles, for example, the sheets may be washed in a liquid comprising the microparticles or the sheets may be sprayed with an aerosol application vehicle containing the microparticles. The application vehicles and treatment methods for applying the microparticles listed above constitute a non-exhaustive list as other possibilities remain and would be covered by the present invention.

While the patient rests or sleeps upon the bed sheet, their body's natural heat and movement erodes the microparticles and releases the therapeutical agent into any exposed areas of the skin in contact with the sheets, such as the arms, legs, back and torso area among others.

In a non-limiting scenario, this application could be used to provide regular doses of therapeutical agents.

The invention defined herein may be used to, for example, reduce and remove persistent odors from animal-related furniture, such as dog beds. In this case, the active ingredient may be a deodorizing agent specially formulated to counteract the general smell of the animal. In this application, the application vehicle may be a paste that is initially spread over the fabric during the manufacture of the furniture. This paste comprises the microparticles and is applied by the manufacturer before shipping. An aerosol spray containing a formulation of microparticles having the same active ingredients may also be provided separately so that the odor-removing functionality of the furniture can be recharged when indicated by a wear indicator. The substrate may be any fabric made of artificial fibers (such as for example, nylon) that is used for the exterior covering of furniture. A solid support is used to apply the paste acting as the application vehicle. In this example, the rollers may be covered with an area of PPFV to which the application vehicle (paste) is applied. The application vehicle (paste) is then pressed onto the fabric, at which point the process is repeated until all of the exposed fabric has been treated. A visible wear indicator may be identified on an area on the fabric, such as a small patch of specially treated fabric that changes color as the active ingredients are gradually exhausted. When the wear indicator shows the active ingredients are exhausted, an aerosol spray may be used to reapply the active ingredients and maintain the odor-neutralizing ability of the treated fabric.

In another non-limiting example, the invention defined herein may be used to apply a skin moisturizer through the application of a bath towel or cloths to a subject's body. In this case, the active ingredient is a moisturizer that rehydrates and protects skin. Further to this case, the application vehicle may be a liquid vehicle that contains the microparticles with the skin moisturizer. In this example, the bath towel is soaked in the liquid vehicle and dried before it is shipped. The microparticles within the application vehicle are electrostatically attracted to the material of the bath towel (which may be cotton, rayon, or polyester among others) and attach themselves to the fibers. If the bath towel is equipped with a wear indicator, the application of the microparticles via the liquid application vehicle causes the indicator to show that the towel has a full charge of skin moisturizer. The subject rubs the towel against their body to dry themselves off. The rubbing motion of the towel against the skin causes the microparticles to erode and the skin moisturizer to be released. Over time, the amount of moisturizer released onto the skin decreases as microparticles in the bath towel are exhausted. Once the microparticles are exhausted, the subjects may replenish the towel by re-soaking it into the liquid application vehicle.

In a further non-limiting example of the present invention, the formulation comprising a color dye and an active ingredient (such as for example, taurine) is prepared as defined herein. The formulation is applied to a sticker-type non-permanent tattoo support in a desired shape or design and then dried. The treated sticker-type tattoo support is applied onto the skin and the formulation (as well as the shape or design) is transferred onto the skin by rubbing the treated sticker-type tattoo support with a damp washcloth. In this specific example, taurine is absorbed transdermally by the skin during the wear period of the tattoo.

According to a further aspect, the present invention relates to formulations of microparticles, application vehicles comprising microparticles and/or treated supports, as defined herein that are provided in kits or commercial packages. Such kits or commercial packages typically comprise instructions indicating for example, how to use the formulations, application vehicles and treated supports, the nature of the active ingredient(s) (if any provided), the recommended uses, the recommended period of time over which the use should be carried out, the expiry date, etc.

It should be understood that the industries and commercial applications identified above constitute a non-exhaustive list and that other commercial applications remain and are intended to be covered by this invention and this application.

The following examples are to illustrate different implementations of the invention defined herein with no intention of restricting the invention to these examples.

XIII. Experiments and Data Analysis

Example 1

Preparation of a Formulation Comprising Microparticles

The following example illustrates the manner of preparation of 20 g of a formulation comprising 10% of microparticles in water, wherein the microparticles comprise 5% Ceramide A as active ingredient, and a binding agent is used to achieve a microparticles:binding agent ratio of 0.5:1. Table 3 indicates the elements and the amounts thereof entering the formulation.

TABLE 3

| Formulation | |
|---|---|
| Elements | Amount in grams (g) |
| PART A | |
| Tripalmitin (100%, TP) [A1] | 1.24 |
| Glycerol monosterate (GMS) (100%) [A2] | 0.38 |
| Paraffin (PARA) (100%) [A3] | 0.28 |
| Ceramide-A (CER) (100%) [A4] | 0.10 |
| PART B | |
| Cetyl trimethylammonium chloride (CTAC) (53%) | 0.19 |
| Water (100%) | 15.59 |
| PART C | |
| TriPoly AC M4445 (PAC) (45%) | 2.22 |
| Total | 20.00 |

Preparation of a Hydrophobic Mixture:

Part a was Prepared in an Aluminum crucible, the mass of which was previously determined [A0] using an analytical balance. The crucible was weighted after addition of each of the elements of PART A: namely, [A1], [A2], [A3] and [A4]. The crucible was then heated in order to melt the elements. The melted elements were stirred with a spatula. The aluminum crucible was then removed from the heat source and was cooled down until the mixture had solidified, at which stage the mass of the aluminum crucible was measured [Atot].

Preparation of PART B:

Part B was prepared into a 50 ml beaker (PYREX™) The empty beaker was weighted prior to addition of the elements [B0] and after addition of each of CTAC [CATC] and water [WATER]. The beaker containing CTAC and water was then heated to between about 60° C. and about 70° C. At this point, the aluminum crucible was heated again so as to melt completely the PART A mixture. Melted PART A was added into PART B and mixed to obtain a coarse emulsion. The mass of the beaker was weighted again [Btot]. The mass of the aluminum crucible was measured [Afin].

Formation of Microparticles by Homogenization:

The coarse emulsion containing PART A and PART B was homogenized one minute using a Silverson™ homogenizer at maximum speed (at around 10 000 rpm). The beaker was cooled down in a water bath at temperatures equal to or inferior of 15° C. and the homogenization was resumed for one minute at minimum speed. The beaker containing the formulation of microparticles was then removed from the water bath.

Addition of a Binding Agent:

The mass of the beaker containing the formulation of microparticles was determined [Bfin]. PART C was then added and mixed manually with the beaker containing PART A and PART B. The mass of the beaker was noted [C].

The formulation of microparticles obtained by this procedure may be applied to a substrate or may be kept into a hermetic container for later use.

Example 2

Transfer of the Formulation of Microparticles onto a Solid Support

Figure 10A:
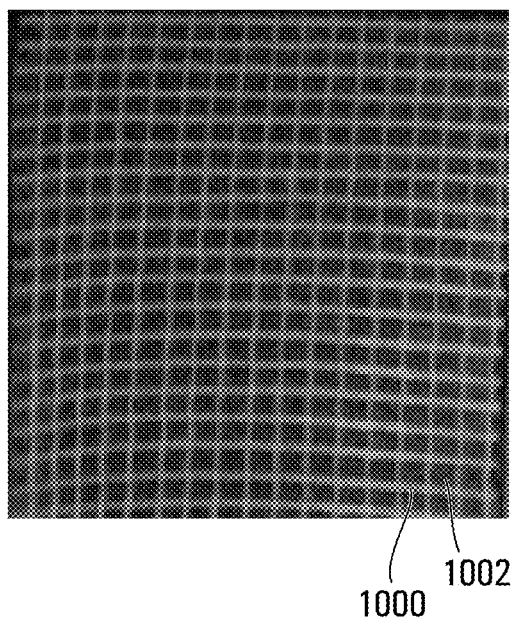
FIGS. 10A and 10B are pictures with a visual indication that a formulation has been applied to a substrate.
Figure 10B:
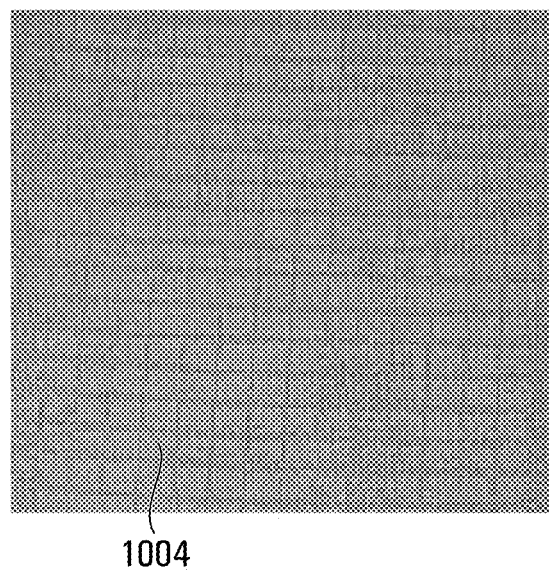

A solid support was prepared using polypropylene (Gemex PPC3119™) (see FIG. 10A, (1002)) and glass fiber (Fiba Tape™) (see FIG. 10A, (1004)) which were assembled together by pressing the two material against each other using pressing rollers (Richeson™ 11" Baby Press) (see for example, FIG. 10A).

The solid support was weighted [S0]. The formulation was applied onto the solid support so as to fill up the recesses defined by the glass fiber net applied onto the polypropylene film. The solid support with the applied formulation was weighted [S1]. The mass of the formulation was determined by calculating the difference ([S1]−[S0]). The formulation was dried until the mass of the formulation in the recesses had diminished by half [S2].

Example 3

Figure 11:
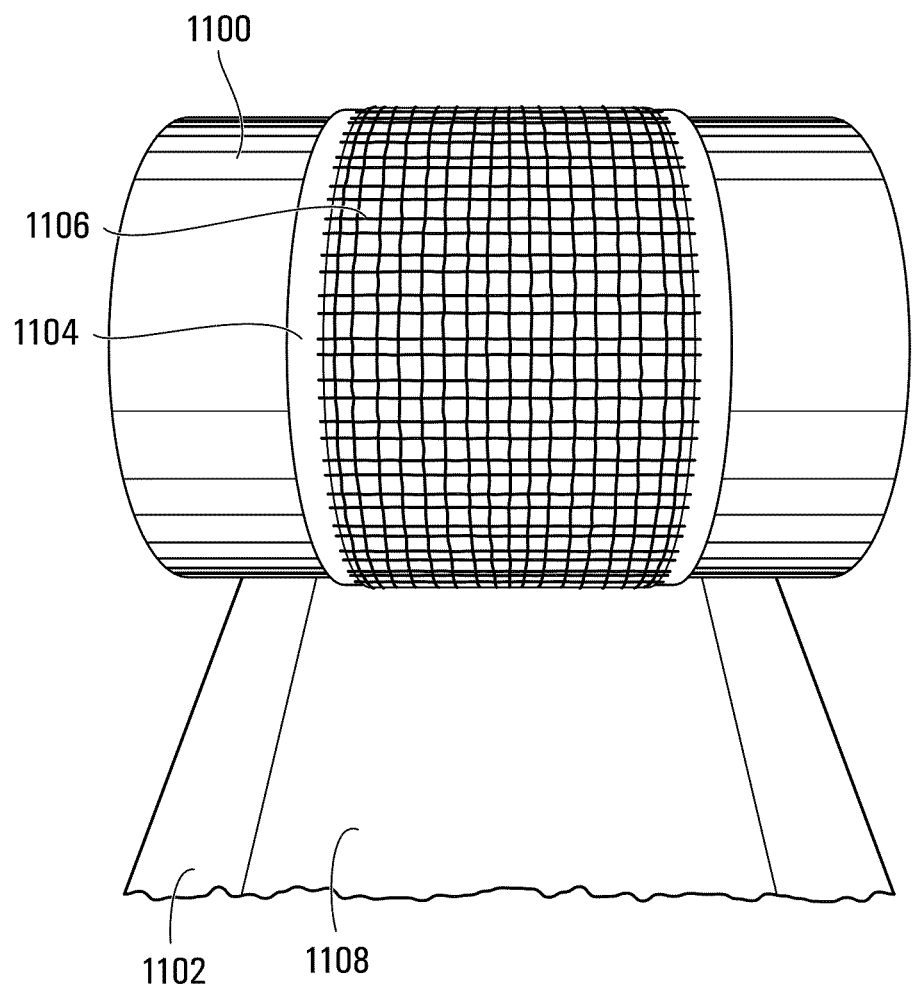
FIG. 11 is a schematic representation of a non-limiting example of a method for transferring a formulation from a PPFV support assembly as in FIG. 10A onto a textile substrate using pressing rollers.

Transferring the Formulation of Microparticles from a Solid Support to a Substrate As shown in FIG. 11, the surface of the textile (substrate) onto which the formulation is to be transferred, should preferably be larger than the surface of the solid support. In this example, pressing rollers (Richeson 11" Baby Press) (1100) are used to transfer the microparticles from the solid support (1104), having a mesh of for example glass fiber (1106), onto a textile (1108).

A foam (1102), preferably having a larger surface than the textile (1108) is applied to the plate onto which the textile is placed (i.e., so as to be in contact with the surface of the substrate that will not be applied with the formulation) to facilitate contact between the formulation on the support (1104) and the textile (1108).

The textile (1108) is weighted [E0] and placed onto the foam (1102). The surface of the textile that will be applied with the formulation should be facing up. The support (1104) having the formulation of microparticles applied thereon is placed onto the textile (1108) so as to place the microparticles in contact with the textile (1108). Optionally, a further foam may be applied between the roller (1100) and the support (1104) (not shown). The press is operated so as to press the sandwich "foam-textile-support" or "foam-textile-support-foam" on its entire length. The foam and the substrate are removed and the treated textile is weighted. The support devoid of formulation is weighted [Sfin]. The treated textile is dried at room temperature with or without application of extra ventilation, such as by using a table fan. Once dried, the textile is weighted [Efin].

FIG. 5 indicates the percent of formulation transferred from a solid support to a rigid-surfaced substrate or to a flexible-surfaced substrate (use of foam). Notably, the percent of formulation transferred is increased when foam is used, indicating that the efficiency of transfer is improved when the substrate is at least partially flexible.

Example 4

Data Analysis

The concentration of microparticles and elements entering in the preparation thereof may be determined using the measurements obtained in the preparation of the formulation comprising the microparticles:

TABLE 4

Determining the concentration of microparticles

| Elements | Amount (%) |
|---|---|
| TP [A1] | 100 * (A1 − A0)/(A4 − A0) |
| GMS [A2] | 100 * (A2 − A1)/(A4 − A0) |
| PARA [A3] | 100 * (A3 − A2)/(A4 − A0) |
| CER [A4] | 100 * (A4 − A3)/(A4 − A0) |

The concentration of microparticles and surfactant in the beaker before addition of the binding agent (initial or "$_i$") may be calculated as follows:

Microparticle (referred to as $\mu Pi$)=(A4−Afin)/(Btot−B0)

CTACi=(CTAC−B0)*0.53/(Btot−B0)

The following formula may be used to determine the concentration of microparticles ($\mu$Pi), surfactant (CTAC) and binding agent (PAC) in the formulation:

TABLE 5

Determining the concentration of microparticles

| | Formula |
|---|---|
| $\mu$Pi % (p/p) | 100 * $\mu$Pi * (Bfin − B0)/(C − B0) |
| PAC, % (p/p) | 100 * PAC * (C − Bfin) * 0.45/(C − B0) |
| CTAC, % (p/p) | 100 * CTACi * (Bfin − B0)/(C − B0) |

The percent efficiency of transfer of the formulation of microparticles from the support to the textile may be calculated as follows:

Waste (%)=100*(Sfin−S0)/(S2−S0)

Transfer (%)=100−Waste

The fraction of each element in the dry material (microparticles, active ingredient, binding agent, and surfactant) remaining on the treated textile may be calculated as follows:

$F_{PAC,dry}$=PAC/(CTAC+PAC+$\mu$Pi)

$F_{CTAC,dry}$=CTAC/(CTAC+PAC+$\mu$Pi)

$F_{\mu Pi,dry}$=$\mu$Pi/(CTAC+PAC+$\mu$Pi)

The surface concentration of each element may be calculated as follows:

$P_{textile}$ (g/m$^2$)=$F_{\mu Pi,dry}$*(Efin−E0)/surface $PAC_{textile}$ (g/m$^2$)=$F_{PAC,dry}$*(Efin−E0)/surface $CTAC_{textile}$ (g/m$^2$)=$F_{CTAC,dry}$*(Efin−E0)/surface wherein the surface is expressed in square meter (m$^2$).

Example 5

Melting of the Microparticles

The temperature at which the microparticles melt may be determined from the formulation remaining on the aluminum crucible (Afin−A0) or may be determined on the treated textile (in the dry state) using a melting point apparatus such as a AT-HLM (Qinc) apparatus or using differential scanning calorimeter or thermal analysis. Methods and apparatus to determine melting temperatures are well known in the art.

Example 6

Testing the Resistance of a Treated Substrate to Wash Cycles

Resistance of a treated textile to wash cycles was assessed by determining the amount of microparticles remaining on the treated textile (or by determining the amount of microparticles released from the treated textile) after consecutive wash cycles.

Testing the resistance of a treated textile to wash cycles was performed in the following conditions:
Detergent=Zero™ (Woolite™);
Concentration of detergent in the washing solution=1 g of Zero™ per liter of water;
Temperature of the washing solution=23° C.;
pH of the washing solution=8.1; and
Temperature of the rinsing water=13° C.;

The procedure includes obtaining a sample of 7 cm×7 cm of a generally flat textile. Generally, the sample may be obtained from a textile which is of commercial interest and which is to enter in the fabrication of an article of manufacture of interest. To avoid raveling of the sample during the test and to prevent loss in sample mass, the edges of the sample are doubled over and sewed using a conventional sewing machine or sewed manually using a needle and a thread. The techniques to sew the edges of a textile to prevent raveling will be well known by those of skill in the art.

If the sample contains a substantial amount of synthetic fibers such as polyester, nylon or the like (e.g., 100% nylon (N100), 65% polyester and 35% cotton (P65C35), 70% nylon and 30% cotton (N70C30), 90% nylon and 10% spandex (N90S10), 100% cotton (C100), 95% cotton and 5% spandex (C95S05), (P100m) and Denim), the edges of the sample may also be welded using a heat source such as a blowtorch, a welding torch or other flame sources.

Only the edges of the sample should be subjected to sewing or welding so that the remaining of the sample is suitable for deposition of a formulation of microparticles. If the edges of the sample are welded, the welded sample should be allowed to cool down before the formulation is applied thereon.

The mass of the sample is weighed, preferably on an analytical balance to the 4$^{th}$ decimal [TS].

The formulation of microparticles as obtained in EXAMPLE 1 was applied to the sample using the techniques as defined in EXAMPLE 2 and EXAMPLE 3. The mass of the treated sample was weighed on an analytical balance to the 4$^{th}$ decimal. The treated sample was then dried at approximately 23° C. for approximately 1½ hour and/or until the mass of the treated sample had diminished by approximately 50%. The water content remaining in the sample may be determined by weighing the sample or by any other suitable method. The mass of the treated sample was determined again using an analytical balance [TSini].

Suitable containers for use in this test have a volume of 500 ml and can be hermetically closed to avoid leakage of the washing solution during the procedure.

A wash cycle consists in filling the container with 250 ml of washing solution as defined above. The washing solution was manually poured into the container. The volume of wash solution poured into the container should preferably be smaller then the volume of the container to allow for movement of the wash solution in the container during the procedure. The treated sample was then placed in the container and the container was closed hermetically.

Figure 12:
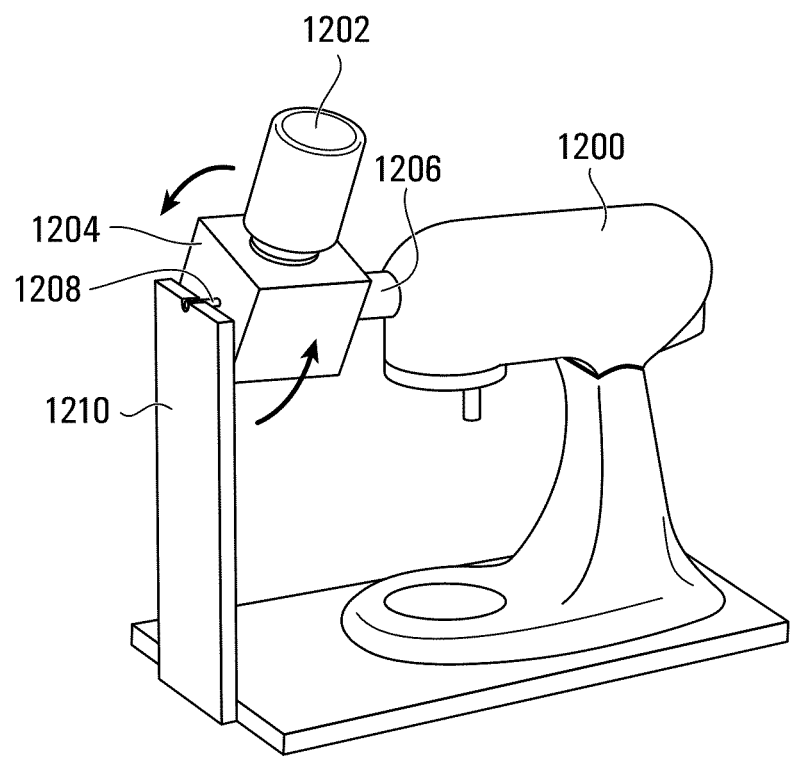
FIG. 12 is a schematic representation of an apparatus used to determine the retention of microparticles on a substrate subjected to wash cycles.

The container was rotated at a frequency of 1 Hz, for 15 minutes so that at the end of the 15-minute rotation period, the container had been through about 90° rotations. To rotate the container, the container was mounted on the rotation axis of a tilt-head stand mixer (obtained from Kitchen-Aid™) having a motor wattage of 325 watts such as illustrated in FIG. 12. The stand mixer (1200) comprises a platform (1204) mounted in the axis of the motor of the stand mixer (1200). One end of the platform is rotably mounted to the stand mixer through the attachment port (1206) of the stand mixer (1200). Optionally, the other end of platform is also rotably mounted on a supporting plate (1210) through a supporting pin (1208) received in a recess in the supporting plate (1210). It will be understood that, in this specific setting, the supporting plate (1210) is required to prevent the stand mixer (1200) from tipping over due to the weight of the platform (1204) and the container (1202) mounted thereon. The container (1202) is attached to the platform (1204) using suitable attachment means such as, but not limited to, elastics, tapes, latches, etc. Any other technique and/or apparatus to rotate the container are also intended to be covered by the present specification.

At the end of the rotation period, the container was open and substantially all of the washing solution was gently removed while preventing the sample from exiting the container. The washing solution was poured into a waste container. The wash solution may be poured manually or by any means to transport the wash solution out of the container such as by using a pipette of suitable size.

The treated sample was then rinsed twice with 250 ml of rinsing water. To rinse, 250 ml of rinsing water was poured into the container. The container was closed hermetically and rotated as described above for about 1 minute. The container was open and substantially all of the rinsing water was poured out of the container and added to the waste container comprising the wash solution. Another 250 ml of rinsing water was added to the container. The container was hermetically closed and rotated for about 1 minute. The container was open and substantially all of the rinsing water was poured out of the container and added to the waste container having the wash solution and the first rinsing water. By "substantially all of the rinsing water" is meant that the inside of the container is visibly free of liquid body.

The treated sample was wrung manually such as by using a rotating salad spinner. The treated sample was rotated in the salad spinner for about 1 minute.

The treated sample was then air-dried at approximately 23° C. for approximately 1½ hour with or without application of extra ventilation provided by a table fan and/or until the treated sample had lost 50% of its initial mass (i.e., 50% of [TSini]). Other methods to determine the water content of the sample may be used. Such techniques and apparatus are well known to those of skill in the art.

To recover any fiber or any material from the sample that may have been lost during the wash cycle, the content of the waste container (i.e., the wash solution and the rinsing solution) may be filtered using conventional methods used in the art, such as for example, by using filters of suitable pore size and a vacuum system. The pores of the filters should be small enough to prevent fibers of the sample to pass though the pores during filtration. The fibers obtained from filtration of the wash and rinse solutions are air-dried at approximately 23° C. for approximately 1½ hour.

The weight of the treated sample (and any material recovered from filtration of the waste solution) is determined to the $4^{th}$ decimal using an analytical balance [TSfin$_{wash\ 1}$]. The weight of microparticles remaining on the sample is determined using the formula:

[TSini]−[TSfin$_{wash\ x}$]=weight of microparticles released during washing $x$;

[TSfin$_{wash\ x}$]−[TS]=weight of microparticles remaining on the sample;

wherein "$x$" indicates the number of wash cycles the sample has been through.

Figure 3A:
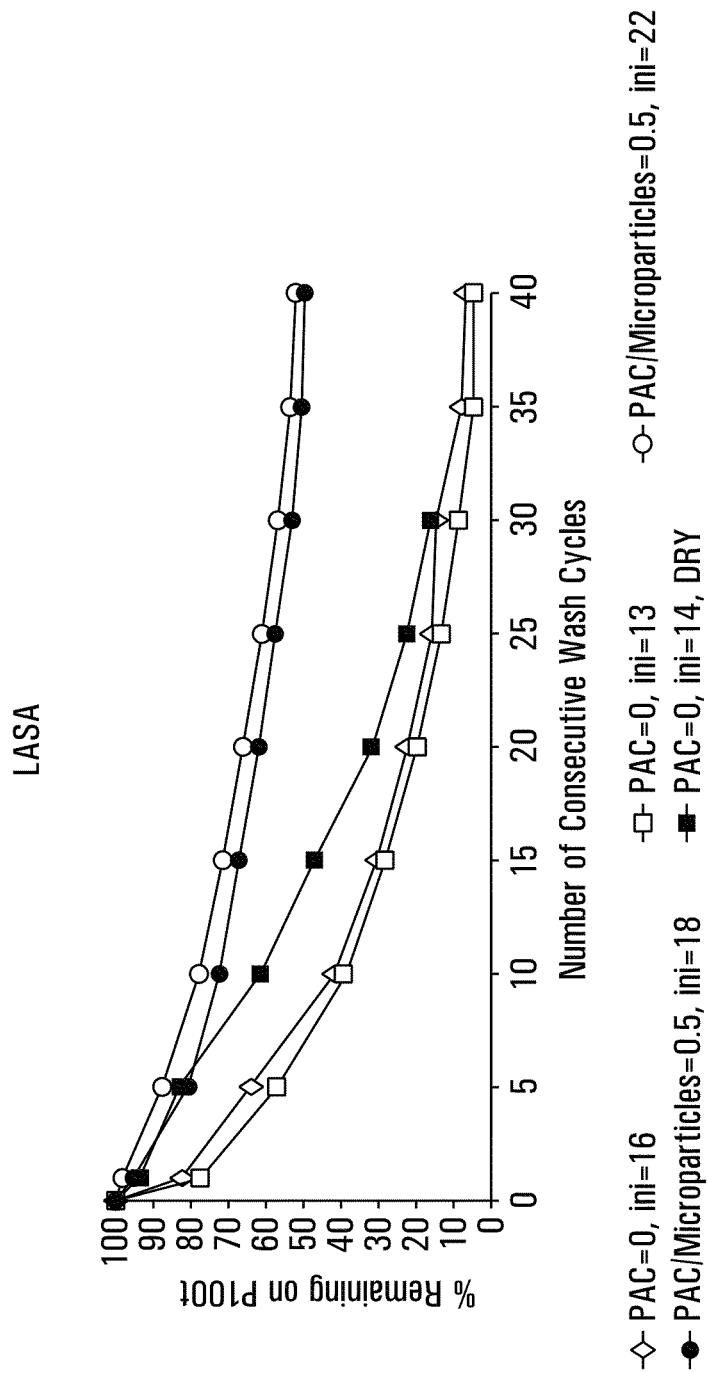
FIGS. 3A to 3C are graphs showing the influence of wash cycles on the retention of microparticles in a P100t substrate.
Figure 3B:
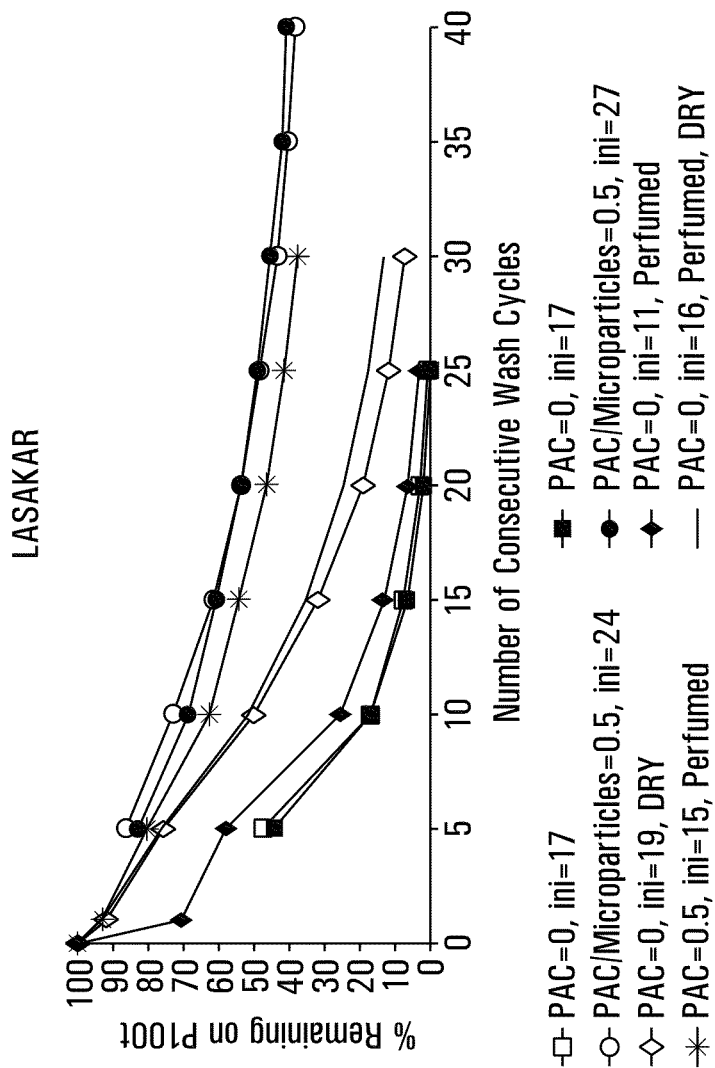
Figure 3C:
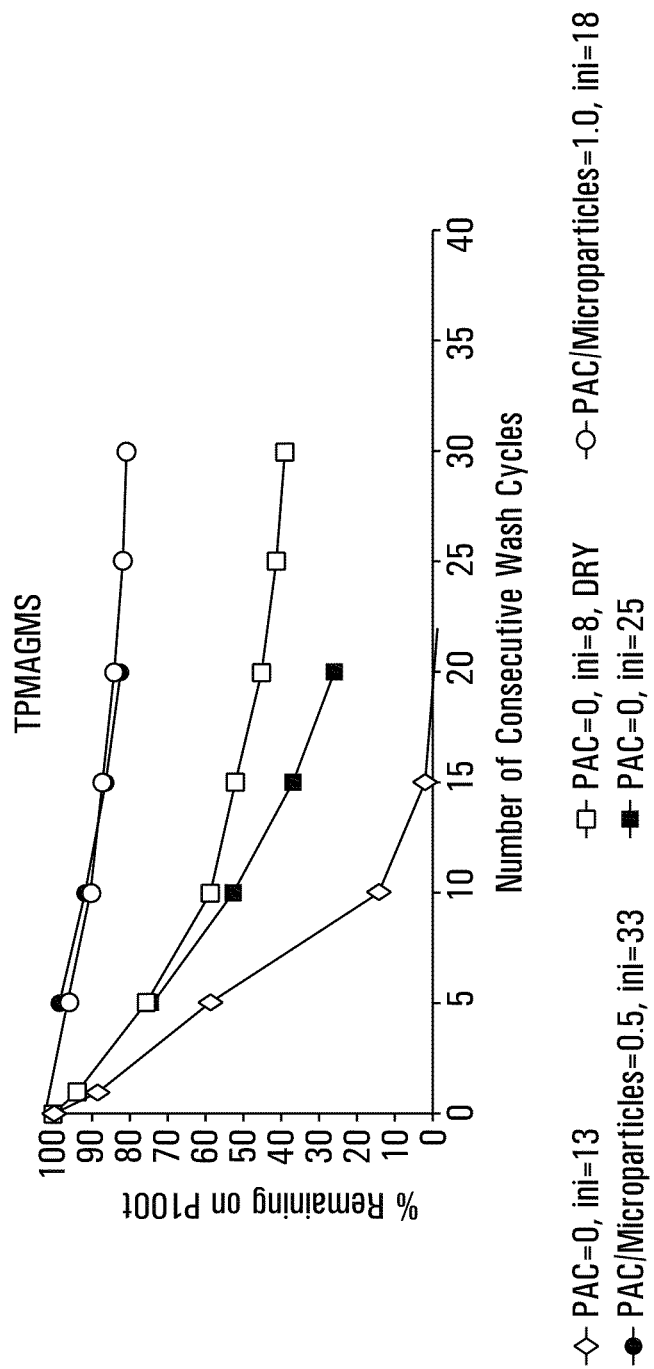

The wash cycle test was repeated at least 40 times (40 wash cycles) for the same sample. The weight of the microparticles remaining on the sample after each wash cycle was determined. The data obtained was plotted as illustrated in FIGS. 3A to 3C. For better accuracy of the results, the test was repeated with 3 other treated samples using the same condition as above. An average of the mass of microparticles remaining on the samples was obtained from the four samples tested and plotted against the number of wash cycles. Not more than one sample should be placed in the same container as the samples may adhere to one another and the results of the test may be corrupted.

FIGS. 3A, 3B and 3C illustrate the percent microparticles remaining on the samples following the indicated number of wash cycles. FIGS. 3A, 3B and 3C also show the influence of a binding agent on the release of microparticles from the treated textile. Table 6 indicates the conditions used in this experiment.

TABLE 6

| | | Experimental conditions | | |
|---|---|---|---|---|
| Formulation | Binding agent | Ratio binding agent/microparticle | Type of Transfer | Total initial (g/m²) |
| LASA | — | 0 | humid | 13 and 16 |
| LASA | PAC | 0.5 | humid | 18 and 22 |
| LASA | — | 0 | dry | 14 |
| LASAKAR | — | 0 | humid | 11, 17 and 17 |
| LASAKAR | PAC | 0.5 | humid | 15, 24 and 27 |
| LASAKAR | — | 0 | dry | 16 and 19 |
| TPMAGMS | — | 0 | humid | 25 |
| TPMAGMS | PAC | 0.5 | humid | 33 |
| TPMAGMS | — | 0 | humid | 13 |
| TPMAGMS | PAC | 1.0 | humid | 18 |
| TPMAGMS | — | 0 | dry | 8 |

As shown in FIG. 3A, after 20 wash cycles approximately 30% of the microparticles obtained from a LASA formulation remained on the textile in the absence of binding agent (PAC=0, ini=14, dry transfer). Addition of a binding agent to the LASA formulation in a ratio of binding agent/microparticles of 0.5 (PAC/microparticles=0.5, ini=18 and PAC/microparticles=0.5, ini=22), increases the percent of microparticles remaining on the substrate to approximately 65% after 20 wash cycles and 55% after 30 wash cycles (FIG. 3A).

As shown in FIG. 3B, for microparticles obtained from a LASAKAR formulation, approximately 25% of microparticles remains on the textile after 20 wash cycles in the absence of binding agent (PAC=0, ini=19, dry transfer and PAC=0, ini=16, Perfumed, dry transfer), this value increases to approximately 45% after 40 wash cycles in the presence of a binding agent, wherein the ratio of binding agent/microparticles is 0.5 (PAC/microparticles=0.5, ini=24 and PAC/microparticles=0.5, ini=27).

FIG. 3C shows that approximately 45% of microparticles obtained from a TPMAGMS formulation remains after 20 wash cycles in the absence of a binding agent (PAC=0, ini=8, dry transfer). Addition of a binding agent in a ratio of binding agent/microparticles is of 1.0 (PAC/microparticles=1.0, ini=18), increases the percent of microparticles remaining on the textile to approximately 85% after 20 wash cycles.

The test allows determining the rate of release of the microparticles from the sample. The data obtained from the test demonstrates that the rate of release of microparticles from the sample is positive and constant at least between 10 and 20 wash cycles and/or constant at least between 20 and 30 wash cycles. A positive rate of release indicates that microparticles and therefore active ingredient dispersed therein are still being released from the sample at least between 10 and 20 wash cycles and/or at least between 20 and 30 wash cycles.

The data also demonstrates that the amount of microparticles released from the sample between 15 and 20 wash cycles is about 2 to about 3 times the amount of microparticles released from the substrate between 30 to 40 wash cycles.

Example 7

Determining the Release Index

Figure 4A:
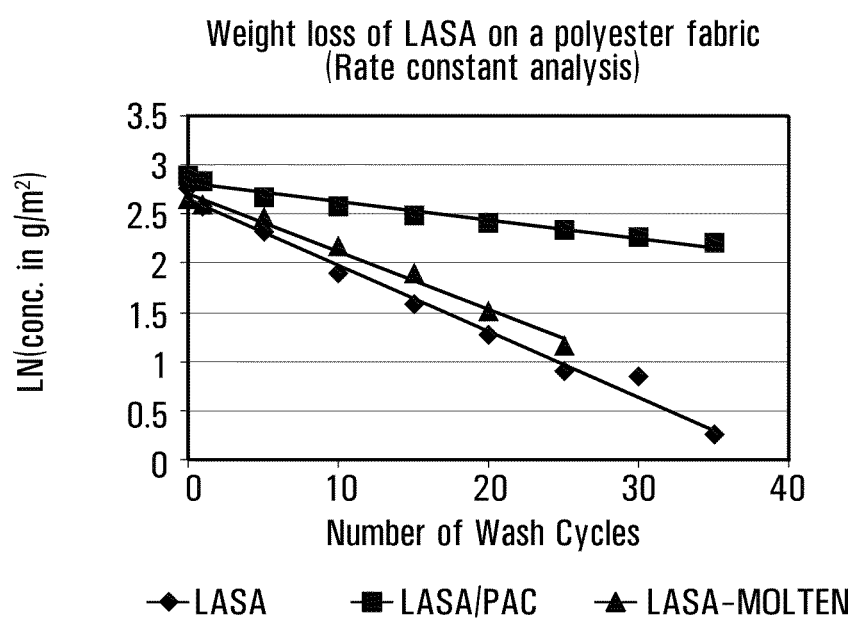
FIGS. 4A to 4C are graphs showing a release rate constant analysis for microparticles obtained from a LASA (FIG. 4A), a LASAKAR (FIG. 4B) and a TPMAGMS (FIG. 4C) formulation.
Figure 4B:
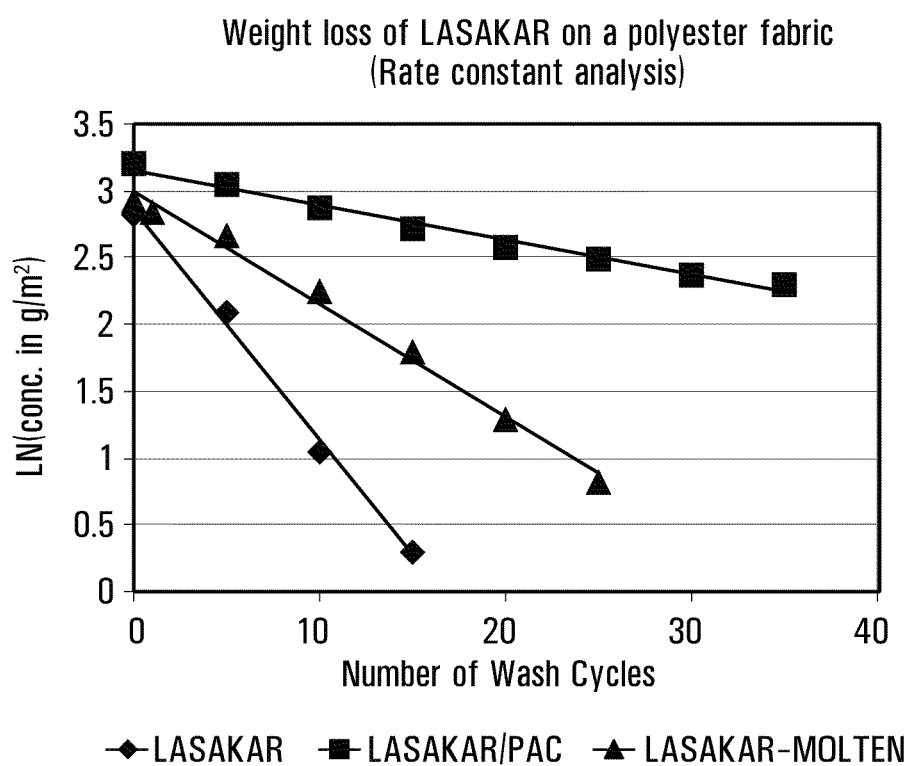
Figure 4C:
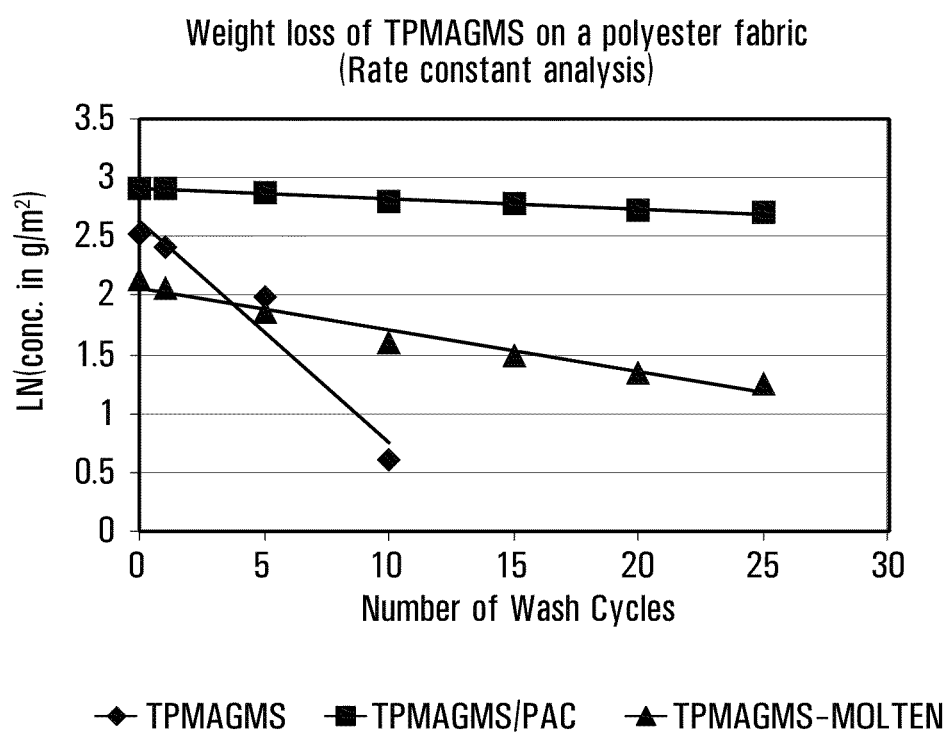
Figure 5:
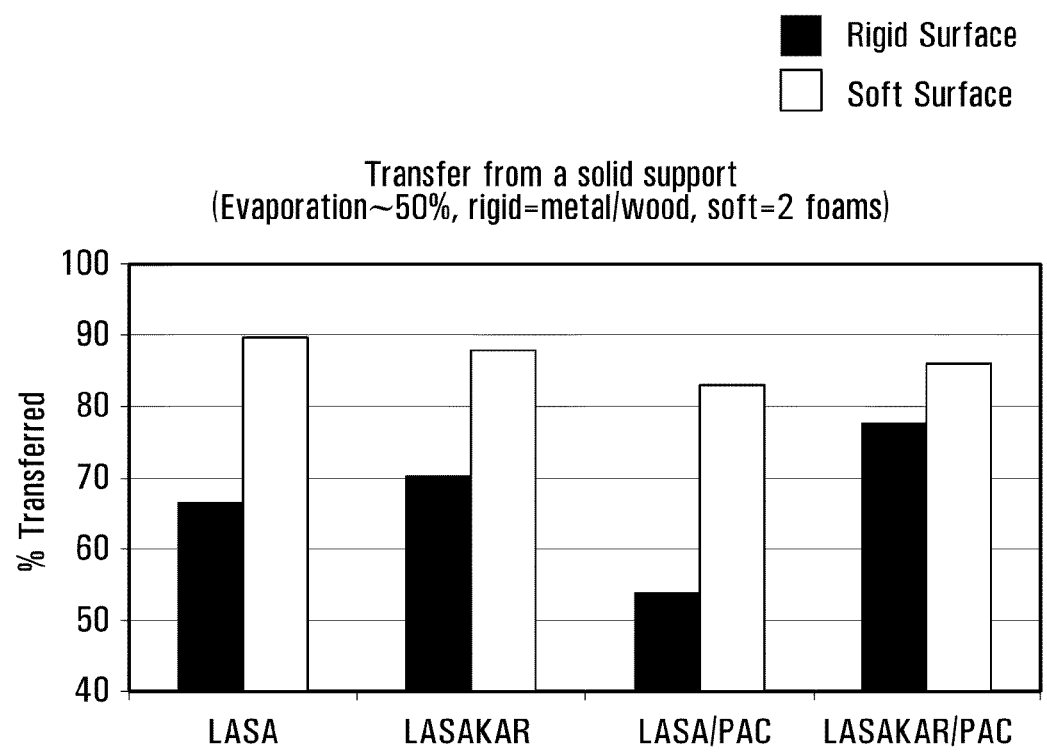
FIG. 5 is a graph indicating the percent of microparticles transferred from a solid support onto either a rigid surfaced substrate or a soft surfaced substrate. Microparticles are obtained from the indicated formulations which may comprise or a binding agent or may be free of binding agent.

The release index is a correlation of the rate of release of microparticles over a determined surface of treated substrate over time (evaluated in terms of number of wash cycles). The rate of release of microparticles obtained from LASA, LASAKAR and TPMAGMS formulations were obtained from the data presented in FIGS. 3A, 3B and 3C. FIG. 4A shows the rate analysis of microparticles obtained from a LASA formulation, FIG. 4B shows the rate analysis of microparticles obtained from a LASAKAR formulation and FIG. 4C shows the rate analysis of microparticles obtained from a TPMAGMS formulation.

Table 7 provides the rate constant and the release index of microparticles obtained from the indicated formulation:

TABLE 7

Release Index

| Formulation | First Order Rate Constant | Release Index (RI) |
|---|---|---|
| LASA | −0.067 | 7 |
| LASA-PAC | −0.019 | 2 |
| LASA-MOLTEN | −0.059 | 6 |
| LASAKAR | −0.173 | 17 |
| LASAKAR-PAC | −0.026 | 3 |
| LASAKAR-MOLTEN | −0.085 | 8 |
| TPMAGMS | −0.189 | 19 |
| TPMAGMS-PAC | −0.009 | 1 |
| TPMAGMS-MOLTEN | −0.036 | 4 |

The release Index is calculated as follow:

Release Index (RI)=Round(−100*rate constant)

The release index indicated in Table 7 corresponds to the kinetic of the release of microparticles in a soapy solution.

The half-life of the microparticles on a substrate such as a textile corresponds to the number of wash cycles required to remove half of the initial amount of microparticles applied to the substrate and is calculated using the following formula:

$T_{1/2}=69/RI$

The data presented in FIGS. 4A to 4C and in Table 7, indicates that the rate at which the microparticles are released (release index) from a substrate is gradual and constant.

Example 8

Transfer of Microparticles from a Substrate onto the Skin

Tests have been performed to assess the efficiency of microparticles transfer from a substrate to human skin as well as to determine the influence of the temperature on the transfer efficiency.

Samples (or patches) of polyester treated with LASA or LASAKAR formulated microparticles with or without a binding agent (PAC; in a ratio of binding agent/microparticles of approximately 0.5) were applied onto the skin for a period of 30 min. The treated polyester samples were placed on three zones of the skin having the following temperatures 31° C., 33° C. and 34° C. and not covering an articulation and/or a joint. The samples were applied on a surface of 25 $cm^2$ in an amount of approximately 8 $g/m^2$ for all the formulations tested except for the LASA/PAC formulation, which was applied at 16 $g/m^2$. The amount of formulation transferred is indicated in FIG. 6.

Figure 6:
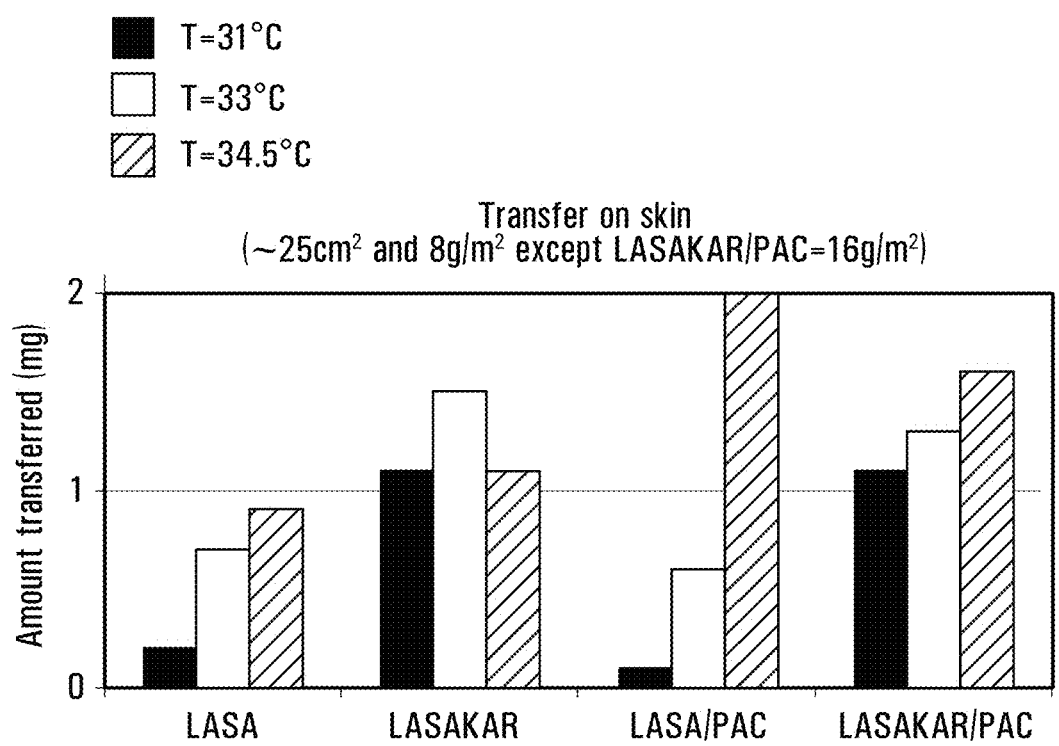
FIG. 6 is a graph showing the influence of temperature on the release of microparticles from a support onto the skin when the microparticles are obtained from the indicated formulations.

FIG. 6 shows, inter alia, that the amount of LASA formulated microparticles transferred increases significantly with an increase in temperature. However, the amount LASAKAR formulated microparticles transferred was similar at all the temperatures tested. This observation may be explained by the fact that this formulation comprises shea butter which partly melts at room temperature. In this experiment, the presence of a binding agent did not significantly influence the transfer.

Example 9

Formulations of Microparticles Comprising Natural Butters

Other formulations were prepared using the elements indicated in Table 8:

TABLE 8

| | | % final | Weight (g) |
|---|---|---|---|
| Formulation comprising natural butters | | | |
| Distilled $H_2O$ | | 84.1 | 107.2067 |
| Surfactant | CTAC 0.3 g/g | 0.7 | 3.0333 |
| [CTAC-30 (30%), Ammonyx, Stepan, Northfield, U.S.] | | | |

TABLE 8-continued

|  |  | % final | Weight (g) |
|---|---|---|---|
| Anti-oxydant | Vitamine E<br>[Oil 28 000 IU (acetate tocopheryl), Life, Toronto, Canada] | 0.2 | 0.2600 |
| Emulsifier | GMS<br>[Cutina, Catalog No. CG83470001, Cognis Oleochemicals Canada Ltd, Mississauga, Canada] | 1.05 | 1.3650 |
| | Formulation comprising microparticles | | |
| Fatty acids | Stearic acid (SA)<br>[Emersol 132, Cat No. N18KXXX124, Cognis Oleochemicals Canada Ltd, Mississauga, Canada Content: 45.5% stearic acid, 50% palmitic acid, 2.5% myristic acid, 1.5% heptadecanoic acid] | 5.85 | 7.6050 |
| | Palmitic acid (PA)<br>[97%, Catalog No. 2712G2-698PNLK0034, Croda, Vaughan, Canada (Palm-Oleo SDN) BHD] | 3.15 | 4.0950 |
| Active ingredients | Olive butter (O)<br>[Catalog No. 2176 New Dimensions Aromatics Inc., Brampton, Canada] | 1.98 | 2.5740 |
| | Mango butter (M)<br>[Catalog No. 3311 New Dimensions Aromatics Inc., Brampton, Canada] | 1.98 | 2.5740 |
| | Grape seed butter (G)<br>[Catalog No. 2174 New Dimensions Aromatics Inc., Brampton, Canada] | 0.495 | 0.6435 |
| | Shea butter (KAR))<br>[Catalog No. 16009-A13 New Dimensions Aromatics Inc., Brampton, Canada] | 0.396 | 0.5148 |
| | Lemon butter (L)<br>[Catalog No. 216F07-01 New Dimensions Aromatics Inc., Brampton, Canada] | 0.099 | 0.1287 |
| Total | | 100 | 130 |

In this particular example, the stearic acid used was composed of 45.5% stearic acid, 50% palmitic acid, 2.5% myristic acid and 1.5% heptadecanoic acid, therefore the final % of stearic acid in the formulation was 2.66%, the final % of palmitic acid in the formulation was 5.3505% [(5.85%×50%)+(3.15%×97% contained in palmitic acid)], the final % of myristic acid in the formulation was 0.146% and the final % of heptadecanoic acid in the formulation was 0.088%.

Combining the Elements—First Procedure:

The fatty acids, butters, GMS and vitamin E were weighted and combined into a first 100 ml beaker (beaker no. 1) (PYREX™). Beaker no. 1 was covered with aluminum foil and placed into a 77° C. incubator until all the elements had melted.

Distilled water and CTAC were combined in a second 200 ml beaker (beaker no. 2) (PYREX™) having a diameter of 5 cm. Beaker no. 2 was covered with aluminum foil and placed in a 77° C. water bath for approximately 15 minutes until the content of beaker no. 1 was completely melted.

Once the content of beaker no. 1 was melted and the content of beaker no. 2 had reached a temperature of 77° C., the content of beaker no. 1 was poured into beaker no. 2.

Combining the Elements—Second Procedure (Alternative to the First Procedure):

All the elements except for CTAC were weighed into a 200 ml beaker having a diameter of 5 cm. The beaker was covered with an aluminum foil and placed into a 77° C. water bath. CTAC was weighed and added to the beaker right before homogenization.

The second procedure presents certain advantages over the first procedure, namely, the melting time of the fatty acids and butters is decreased compared to the first procedure and waste of elements is minimized as the second procedure does not require transfer from beaker to beaker. The formulation does not appear to be affected by which of the first or second procedure is carried out.

Homogenization:

A Sylverson™ L4R homogenizer (Sylverson L4R, Sylverson Machines Ltd., Chesham, UK) equipped with a square hole high sheer screen work head was used for homogenization. While carrying the first (or the second procedure), the homogenizer was pre-heated by immersing the mixing head of the homogenizer into boiled distilled water. The mixing head was then activated to liberate air bubbles that may have been trapped into the system.

For homogenization, the beaker having the formulation was placed into a water bath so as to maintain the formulation at a temperature of about 68° C. during the homogenization step. The homogenizer was set at a speed of 11 500 rpm and the formulation was homogenized for between about 4 to about 6 minutes (the formulation could be homogenized for about 2 to about 16 minutes). Speed of around 7 300 rpm could also be used to obtain formulations having the desired thickness.

Microscopy:

The size of the microparticles was monitored during and after homogenization using a microscope Olympus CX-30. Microparticles having a circular shape, a smooth texture, showing a homogeneous dispersion throughout the formulation and having a size of between about 2 to about 20 microns were observed. It was also observed that the faster the speed at which a formulation is homogenized, the smaller the size of the microparticles obtained.

Cooling:

Following homogenization, the formulation was cooled at room temperature (approximately 21° C.) with occasional manual stirring. The rate of cooling was measured to be approximately 1° C./min.

Other cooling procedures may also be used. Namely, the formulation can be cooled in a water bath having a temperature of approximately 15° C. The formulation may be cooled using a copper coil in which water (approximately 20° C.) circulates. A rate of cooling of about 1.5° C./min can be achieved with the latter procedure.

Thickness:

Thickness of the formulation was established according to known or recognized visual parameters, namely a formulation showing a thickness that is similar to a lotion was attributed the value "0", a formulation showing a thickness similar to mustard was attributed a value of "1", a formulation showing a thickness similar to butter (at room temperature) was attributed the value "2", a formulation showing a thickness similar to whipped butter was attributed a value of "3", a formulation showing a thickness similar firm cream was attributed with a value of "4" and a formulation showing a thickness similar to lard was attributed with a value of "5". The formulation obtained with the elements as indicated in Table 8 showed a thickness of 4.

Example 10

Other Formulations

Other formulations having the composition indicated in Table 10 below were prepared and were tested for the indicated parameters. In Table 10, "SA" refers to stearic acid, "PA" refers to palmitic acid, "LA" refers to lauric acid, "O" refers to olive butter, "M" refers to mango butter, "G" refers to grape seed butter, "KAR" refers to shea butter, "L" refers to lemon butter and "GMS" refers to glycerol monostearate.

The thickness of the formulations is as defined in Example 8.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All published documents mentioned in the above specification are herein incorporated by reference.

The invention claimed is:

1. A method for delivering an active ingredient to a living subject, comprising:
 a) obtaining a formulation of hydrophobic microparticles, the hydrophobic microparticles having a body, the body comprising a central part having an outer surface, wherein the outer surface is substantially hydrophobic, the central part and its substantially hydrophobic outer surface including a non-crosslinked carrier material throughout which is dispersed the active ingredient, wherein the non-crosslinked carrier material includes one or more of a fatty acid-based lipid, a fatty acid, a phospholipid, a wax, a sterol, and a glyceride;
 b) transferring the formulation of hydrophobic microparticles to a substrate; and
 c) placing the substrate in contact with the living subject; wherein the temperature, pH, or both of the living subject triggers progressive erosion of the substantially hydro-

TABLE 8

Formulations

| Formulation | rpm | Time hom min | Rate cooling ° C./min | Thickness | Temp Ini ° C. | Temp hom ° C. | Size μm | Temp fusion ° C. | GMS % | Temp cooling |
|---|---|---|---|---|---|---|---|---|---|---|
| SAPAOMGKARL-GMS | 3 | 6 | −1.1 | 1 | 66 | 64 | <20 | 45.7 | 7 | RT |
| SAPAOMGKARL-GMS | 3 | 6 | −0.62 | 2 | 65 | 60 | <20&<40 | 46 | 7 | RT |
| SAPAOMGKARL-GMS | 3 | 6 | −0.59 | 2 | — | — | 20 < 40 | 45.4 | 8 | RT |
| SAPAOMGKARL-GMS | 6 | 6 | −1.2 | 3 | 69 | 68 | 5 < 20 | — | 7 | RT |
| SAPAOMGKARL-GMS | 7 | 6 | −0.7 | 3 | 69 | 69 | 5 < 15 | — | 7 | RT |
| SAPAOMGKARL-GMS | 7 | 6 | −2.4 | 3 | 69 | 69 | 7 < 15 | — | 7 | RT |
| SAPAOMGKARL-GMS | 7 | 6 | −0.8 | 4 | 68 | 68 | 5 < 20 | — | 7 | RT |
| SAPAOMGKARL-GMS | 7 | 6 | −0.95 | 4 | 68 | 64-68 | 5 < 15 | — | 7 | RT |
| SAPAOMGKARL-GMS | 7 | 2 | −0.97 | 4 | 69 | 65-69 | 5 < 15 | — | 7 | RT |
| SAPAOMGKARL-GMS | 7 | 4 | −1.36 | 1-3 | 66 | 65-66 | 5 < 15 | — | 7 | RT |
| SAPAOMGKARL-GMS | 7 | 6 | −1.36 | 2-3 | 66 | 60-67 | 5 < 20 | — | 7 | RT |
| SAPAOMGKARL-GMS | 7 | 6 | −0.72 | 1-2 | 67 | 70-71 | 5 < 15 | — | 5 | RT |
| SAPAOMGKARL-GMS | 7 | 6 | −1.08 | 3 | 70 | 70 | 4 < 20 | — | 7 | RT |
| SAPAOMGKARL-GMS | 7 | 4 | −1.3 | 3.5 | 71 | 70 | 4 < 20 | — | 7 | RT |
| SAPALAOMGKARL-GMS | 7 | 6 | −1.07 | 4 | 70 | 70-68.5 | 4 < 20 | — | 7 | RT |
| SAPALAOMGKARL-GMS | 4 | 4 | −1.4 | 3 | 72 | 72-73.5 | 4 < 20 | — | 7 | RT |
| SAPAOMGKARL-GMS | 7 | 4 | −0.95 | | — | — | 4 < 15 | — | 7 | RT |
| SAPA-GMS | 7 | 4 | −0.77 | 1.5 | 68 | 66-68 | 4 < 15 | — | 7 | RT |
| SAPAOMGKARLV-GMS | 7 | 4 | — | 4 | — | — | 1 < 15 | — | 7 | RT | rpm = rotation per minute
Time hom min = homogenization time in minute
Rate Cooling ° C./min = rate of cooling of the formulation in Celsius per minute
Thickness = thickness of the formulation
Temp Ini ° C. = initial temperature of the formulation in Celsius
Temp homo ° C. = temperature in Celsius of the formulation when homogenization is carried out
Size μm = size of the microparticles in μm
Temp fusion ° C. = fusion temperature
GMS % = percent GMS present in the formulation
Temp cooling ° C. = cooling temperature
RT = room temperature, approximately 21° C.
— = not determined phobic outer surface and the subsequent progressive erosion of the central part to release the non-crosslinked carrier material and the active ingredient for delivery to the living subject;

wherein at least a portion of the substantially hydrophobic outer surface of the central part is exposed to the environment exterior to the hydrophobic microparticles when the substrate is in a pre-usage, stored state; and wherein the formulation optionally comprises a cationic surfactant, the cationic surfactant being present in the formulation, exterior to the microparticles.

2. A method as defined in claim 1, wherein friction between the substrate and the living subject further triggers the progressive erosion of the substantially hydrophobic outer surface and the subsequent progressive erosion of the central part of the body of the microparticle.

3. A method as defined in claim 1, wherein the substrate is composed of a material selected from the group consisting of woven materials, a non-woven materials, fibrous textiles, non-fibrous textile, fabrics, synthetic materials, papers and paper products, products made from composites, products made from polymers, products made from wood or wood by-products, products made from carbon fiber, products made from glass fiber and synthetic foam.

4. A method as defined in claim 1, wherein the non-crosslinked carrier material is caproic acid, caprylic acid, capric acid, undecanoic acid, lauric acid, tridecanoic acid, myristic acid, pentadecanoic acid, palmitic acid, heptadecanoic acid, stearic acid, oleic acid, elaidic acid, linoleic acid, linolenic acid, arachidic acid, arachidonic acid, a fatty acid derivative, tripalmitin, tristearin or glycerol monostearate or any combination thereof.

5. A method as defined in claim 1, wherein the non-crosslinked carrier material includes a fatty alcohol.

6. A method as defined in claim 1, wherein the non-crosslinked carrier material includes an emollient.

7. A method as defined in claim 1, wherein the formulation further comprises a binding agent.

8. A method as defined in claim 7, wherein the binding agent is a polyacrylic (PAC), a polyurethane (PU), a polysiloxane (POL), a polyvinylpyrrolidone (PVP), a guar gum or an acrylic base or any combination thereof.

9. A method as defined in claim 1, wherein one or more of the hydrophobic microparticles have a size in the range from about 0.1 μm and about 200 μm.

10. A method as defined in claim 1, wherein the hydrophobic microparticles have a melting temperature between about 20° C. and about 60° C.

11. A method as defined in claim 1, wherein the hydrophobic microparticles have a release index between 2 and 7.

12. A method as defined in claim 1, the body being entirely made of a mixture of the non-crosslinked carrier material and the active ingredient, wherein the non-crosslinked carrier material and the active ingredient are uniformly distributed throughout the body.

13. A method as defined in claim 1, wherein the hydrophobic microparticles have a melting temperature between 31° C. and 34.5° C.

14. A method as defined in claim 1, wherein the formulation of hydrophobic microparticles forms a perception indicator on the substrate.

15. A method as defined in claim 14, wherein the perception indicator is a) a visual indicator; b) a wear indicator; or c) a combination of a) and b).

16. The method of claim 1, wherein transferring the formulation of hydrophobic microparticles from the substrate to the living subject is effected by a dry transfer.

17. A method as defined in claim 1, wherein the active ingredient is a therapeutic agent.

18. A method as defined in claim 1, wherein the active ingredient is a cosmetic agent.

* * * * *